United States Patent
Reiffenrath et al.

(10) Patent No.: US 6,689,291 B1
(45) Date of Patent: *Feb. 10, 2004

(54) LIQUID-CRYSTALLINE MEDIUM

(75) Inventors: Volker Reiffenrath, Rossdorf (DE); Detlet Pauluth, Ober-Ramstadt (DE); Herbert Plach, Darmstadt (DE)

(73) Assignee: Merck Patent Gesellschaft mit Beschrankter Haftung, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 08/225,267

(22) Filed: Apr. 8, 1994

(30) Foreign Application Priority Data

Apr. 9, 1993 (DE) ............................................ 43 11 780
Apr. 21, 1993 (DE) ........................................... 43 12 968

(51) Int. Cl.$^7$ ............................................... C09K 19/00
(52) U.S. Cl. ......................... 252/299.63; 252/299.66; 349/182
(58) Field of Search ..................... 252/299.63, 299.66

(56) References Cited

U.S. PATENT DOCUMENTS

| | | | | |
|---|---|---|---|---|
| 4,211,666 A | * | 7/1980 | Inukai et al. | 252/299.6 X |
| 4,910,350 A | * | 3/1990 | Tanaka et al. | 570/129 |
| 5,032,313 A | * | 7/1991 | Goto et al. | 252/299.63 |
| 5,308,537 A | * | 5/1994 | Coates et al. | 252/299.6 |
| 5,324,449 A | * | 6/1994 | Kurmeier et al. | 252/299.01 |
| 5,330,679 A | * | 7/1994 | Sasaki et al. | 252/299.63 |
| 5,342,546 A | * | 8/1994 | Sato et al. | 252/299.6 |

* cited by examiner

Primary Examiner—Cynthia H. Kelly
(74) Attorney, Agent, or Firm—Millen, White, Zelano & Branigan, P.C.

(57) ABSTRACT

A liquid-crystalline medium based on a mixture of polar compound shaving positive dielectric anisotropy, characterized in that it contains one or more fluorophenylcyclohexene derivatives of the formula I

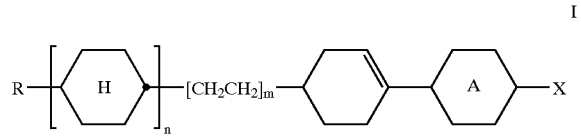

in which R is H, an unsubstituted alkyl or alkenyl radical having up to 18 carbon atoms, in which one or more non-adjacent $CH_2$ groups are optionally replaced by —O—, —S—, —CO—, —O—CO—, —CO—O— or —C≡C—,

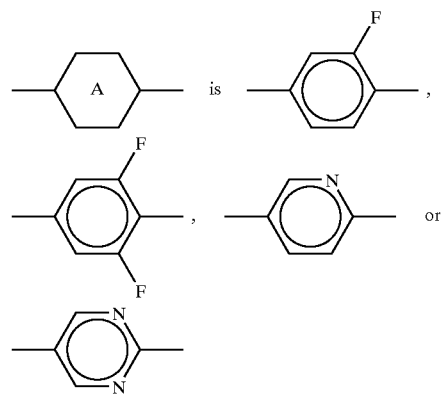

X is CN or Q—Y,
Y is H, F or Cl,
Q is —$CF_2$—, —CHF—, —$OCF_2$—, —OCHF—, —$OCH_2CF_2$—, —CH=CF—, —CF=CH—, —CF=CF—, —O—CF=CF—, —O—CH=CF— or a single bond,
m is 0 or 1, and
n is 0, 1 or 2.

13 Claims, No Drawings

LIQUID-CRYSTALLINE MEDIUM

BACKGROUND OF THE INVENTION

The present invention relates to a liquid-crystalline medium, to the use thereof for electro-optical purposes, and to displays containing this medium, and to novel compounds.

The main use of liquid crystals is as dielectrics in display devices since the optical properties of such substances can be affected by an applied voltage. Electro-optical devices based on liquid crystals are extremely well known to persons skilled in the art and may be based on various effects. Examples of devices of this type are cells having dynamic scattering, DAP cells (deformation of aligned phases), guest/host cells, TN cells having a twisted nematic structure, STN cells ("supertwisted nematic"), SBE cells ("superbirefringence effect") and OMI cells ("optical mode interference"). The most common display devices are based on the Schadt-Helfrich effect and have a twisted nematic structure.

The liquid-crystal materials must have good chemical and thermal stability and good stability towards electrical fields and electromagnetic radiation. Furthermore, the liquid-crystal materials should have low viscosity and give short addressing times, low threshold voltages and high contrast in the cells. Furthermore, at customary operating temperatures, i.e., in the broadest possible range above and below room temperature, they should have a suitable mesophase, for example, a nematic or cholesteric mesophase for the abovementioned cells. Since liquid crystals are generally used as mixtures of a plurality of components, it is important that the components are readily miscible with one another. Further properties, such as electrical conductivity, dielectric anisotropy and optical anisotropy, must meet various requirements depending on the cell type and the area of application. For example, materials for cells having a twisted nematic structure should have positive dielectric anisotropy and low electrical conductivity.

For example, the media desired for matrix liquid-crystal displays containing integrated nonlinear elements for switching individual pixels (MLC displays) are those having high positive dielectric anisotropy, broad nematic phases, relatively low birefringence, very high specific resistance, good UV and temperature stability of the resistance and low vapor pressure.

Matrix liquid-crystal displays of this type are known. Examples of nonlinear elements which can be used to individually switch the individual pixels are active elements (i.e. transistors). This is then referred to as an "active matrix", and a differentiation can be made between various types, for example:

1. MOS (metal oxide semiconductor) transistors and
2. thin-film transistors (TFTs).

The use of monocrystalline silicon as a substrate material limits the display size since even the modular assembly of the various part displays results in problems at the joints.

In the case of type 1, as in the case of the more promising type 2, which is preferred, the electro-optical effect used is usually the TN effect. In the case of type 2, a differentiation is made between two technologies: TFTs comprising compound semiconductors, such as, for example, CdSe, or TFTs based on polycrystalline or amorphous silicon. Intensive research efforts are being made worldwide in the latter technology.

The TFT matrix is applied to the inside of one glass plate of the display, while the inside of the other glass plate carries the transparent counterelectrode. Compared with the size of the pixel electrode, the TFT is very small and has virtually no adverse effect on the image. This technology can also be extended to fully color-compatible image displays, in which a mosaic of red, green and blue filters is arranged in such a manner that each filter element is located opposite a switchable image element.

The TFT displays usually operate as TN cells with crossed polarizers in transmission and are illuminated from the back.

The term MLC display here covers any matrix display containing integrated nonlinear elements, i.e., in addition to the active matrix, also displays containing passive elements such as varistors or diodes (MIM=metal-insulator-metal).

MLC displays of this type are particularly suitable for TV applications (for example pocket TV sets) or for high-information displays for computer applications (laptops) and in automobile or aircraft construction. In addition to problems with respect to the angle dependence of the contrast and the response times, problems result in MLC displays due to inadequate specific resistance of the liquid-crystal mixtures [TOGASHI, S., SEKIGUCHI, K., TANABE, H., YAMAMOTO, E., SORIMACHI, K., TAJIMA, E., WATANABE, H., SHIMIZU, H., Proc. Eurodisplay 84, September 1984: A 210–288 Matrix LCD Controlled by Double Stage Diode Rings, p. 141 ff, Paris; STROMER, M., Proc. Eurodisplay 84, September 1984: Design of Thin Film Transistors for Matrix Adressing [sic] of Television Liquid Crystal Displays, p. 145 ff, Paris]. As the resistance decreases, the contrast of an MLC display worsens and the problem of "after image illumination" may occur. Since the specific resistance of liquid crystal mixture generally decreases over the life of an MLC display due to interaction with the internal surfaces of the display, a high (initial) resistance is very important to give acceptable service lives. In particular in the case of low-voltage mixtures, it was hitherto not possible to achieve very high specific resistances. It is furthermore important that the specific resistance increases as little as possible with increasing temperature and after heating and/or exposure to UV radiation.

In particular in the case of high-resolution MLC displays, the use of materials from the prior art can have a considerable adverse effect on the image quality due to the occurrence of reversed tilt domains [E. Takahashi et al., Proc. 16th Japan. Liq. Cryst. Conference (1990), 212–213]. The MLC displays of the prior art do not meet current requirements.

It has hitherto been possible to prepare liquid-crystalline media having birefringence and phase range values necessary for practical use (for example clearing point of $\geq 70°$) and having threshold voltages of only about 1.8 volts if values of about 98% for the holding ratio under extreme conditions (for example after UV exposure) are desired.

Thus, there continues to be a great demand for MLC displays having very high specific resistance and at the same time a broad operating temperature range, short response times and low threshold voltage which do not have these disadvantages or only do so to a lesser extent.

For TN (Schadt-Helfrich) cells, media are desired which facilitate the following advantages in the cells:

broadened nematic phase range (in particular down to low temperatures), switchability at extremely low temperatures (outdoor use, automobiles, avionics), increased stability to UV radiation (longer life).

The media available from the prior art do not make it possible to achieve these advantages while simultaneously retaining the other parameters.

For supertwisted (STN) cells, media are desired which have a greater multiplexing ability and/or lower threshold voltages and low rotational viscosity and/or low frequency dependence of ε and/or broader nematic phase ranges (in particular at low temperatures). To this end, a further extension of the parameter latitude available (clearing point, smectic-nematic transition or melting point, viscosity, dielectric values, elastic values) is urgently desired.

Fluorophenylcyclohexene derivatives of the formulae

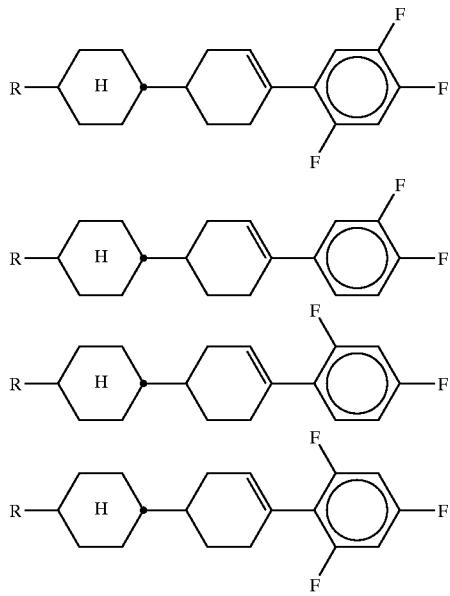

are disclosed in JP 58/018326, JP 57/154136, JP 58/018326, JP 59/082323A and JP 58/198428A.

DE 41 11 765 describes tetra- and pentafluorophenylcyclohexene derivatives of the formula

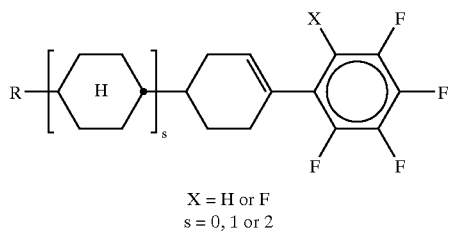

X = H or F
s = 0, 1 or 2

DE 41 13 424 C1 mentions the compound

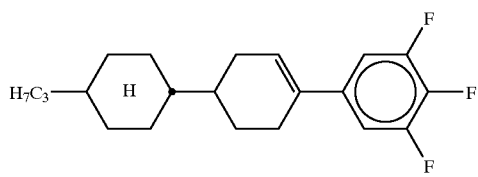

as an intermediate.

DE 40 35 509 mentions compounds of the formulae

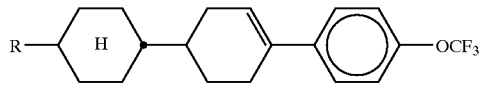

-continued

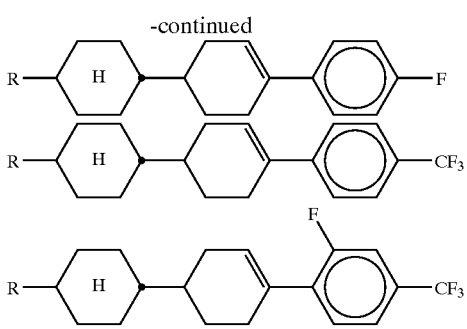

Compounds of the formula

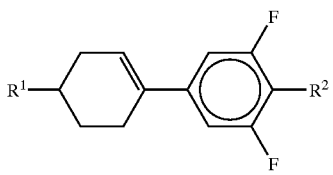

in which $R^1$ is trans-4-alkylcyclohexyl, and $R^2$ is H, CN, halogen or alkyl, are disclosed in JP 05/058928.

JP 04/099739 describes fluorine-containing cyclohexene derivatives of the formula

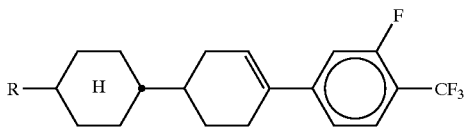

SUMMARY OF THE INVENTION

The object of the invention is to provide media, in particular for MLC, TN or STN displays of this type, which do not have the abovementioned disadvantages or only do so to a lesser extent, and preferably simultaneously have very high specific resistances and low threshold voltages.

It has now been found that this object can be achieved if media according to the invention are used in displays.

In particular, it has surprisingly been found that the media according to the invention exhibit significantly greater surface tilt angles., and the interfering occurrence of reversed tilt domains in MLC displays is thus substantially suppressed. The image quality of the displays according to the invention is thus significantly improved.

The invention thus relates to a liquid-crystalline medium based on a mixture of polar compounds having positive dielectric anisotropy, characterized in that it contains one or more compounds of the general formula I

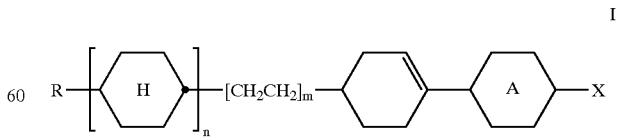

in which

R is H, an unsubstituted alkyl or alkenyl radical having up to 18 carbon atoms, in which one or more non-adjacent $CH_2$ groups may be replaced by a radical selected from the group consisting of —O—, —S—, —CO—, —O—CO—, —CO—O— and —C≡C—,

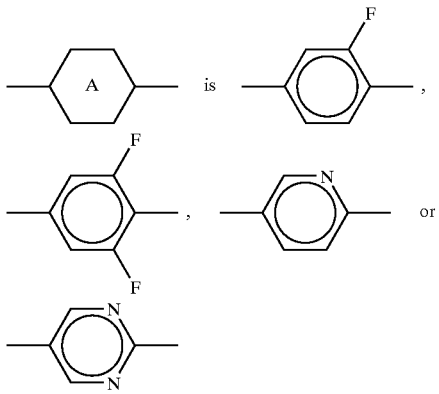

X is CN or Q—Y, where
Y is H, F or Cl and
Q is —CF$_2$—, —CHF—, —OCF$_2$—, —OCHF—, —OCH$_2$CF$_2$—, —CH=CF—, —CF=CH—, —CF=CF—, —O—CH=CF— or a single bond,
m is 0 or 1, and
n is 0, 1 or 2.

The fluorophenylcyclohexene derivatives of the formula I have significantly better stability on exposure to UV or heat than the corresponding unfluorinated or monofluorinated compounds. Compared with the corresponding hydrogenated compounds, they have a higher Δε, which results in surprisingly low threshold voltages in mixtures containing compounds of the formula I.

The invention also relates to electro-optical displays (in particular STN or MLC displays having two plane-parallel outer plates which, together with a frame, form a cell, integrated nonlinear elements for switching individual pixels on the outer plates, and a nematic liquid-crystal mixture of positive dielectric anisotropy and high specific resistance located in the cell) which contain media of this type, and to the use of these media for electro-optical purposes.

The invention likewise relates to novel compounds.

The liquid-crystal mixtures according to the invention facilitate a significant broadening of the parameter latitude available.

The achievable combinations of clearing point, viscosity at low temperature, thermal and UV stability and dielectric anisotropy or threshold voltage are far superior to the previous materials from the prior art.

The requirement for a high clearing point, a nematic phase at −40° C. and a high Δε was previously only achievable to an unsatisfactory extent. Although systems such as, for example, ZLI-3119 have a comparable clearing point and comparatively favorable viscosities, they have, however, a Δε of only +3.

Other mixture systems have comparable viscosities and values of Δε, but only have clearing points in the region of 60° C.

The liquid-crystal mixtures according to the invention make it possible simultaneously to achieve low viscosities at low temperatures (≦600, preferably ≦550 mPa·s at −30° C.; ≦1,800, preferably ≦1,700 mPa·s at −40° C.) and dielectric anisotropy values Δε of ≧3.5, preferably ≧4.0, clearing points above 65°, preferably above 70°, and a high value for the specific resistance, which allows excellent STN and MLC displays to be achieved.

It goes without saying that a suitable choice of components of the mixtures according to the invention also allows higher clearing points (for example, above 90°) to be achieved at higher threshold voltages or lower clearing points to be achieved at lower threshold voltages while retaining the other advantageous properties. The MLC displays according to the invention preferably operate in the first transmission minimum of Gooch and Tarry [C. H. Gooch and H. A. Tarry, Electron. Lett. 10, 2–4, 1974; C. H. Gooch and H. A. Tarry, Appl. Phys., Vol. 8, 1575–1584, 1975]; in this case, a lower dielectric anisotropy is sufficient in addition to particularly favourable electro-optical properties, such as, for example, low gradient of the characteristic line and low angle dependence of the contrast (German Patent 30 22 818) at the same threshold voltage as in an analogous display at the second minimum. This allows significantly higher specific resistances to be achieved in the first minimum using the mixtures according to the invention than using mixtures containing cyano compounds. A person skilled in art can use simple routine methods to establish the birefringence necessary for a prespecified layer thickness of the MLC display through a suitable choice of the individual components and their proportions by weight.

The viscosity at 20° C. is preferably ≦25 mPa·s. The nematic phase range is preferably at least 70°, in particular at least 80°. This range preferably extends at least from −30° to +70°.

Measurements of the "voltage holding ratio" (HR) [S. Matsumoto et al., Liquid Crystals 5, 1320 (1989); K. Niwa et al., Proc. SID Conference, San Francisco, June 1984, p. 304 (1984); G. Weber et al., Liquid Crystals 5, 1381 (1989)] have shown that mixtures according to the invention containing compounds of the formula I exhibit a considerable decrease in the HR with increasing temperature.

The media according to the invention are distinguished by extremely favorable elastic constants and very favorable viscosity values in addition to an unusually broad nematic phase range, resulting, in particular when used in STN displays, in significant advantages over prior-art media.

The media according to the invention are preferably based on a plurality of (preferably two or more) compounds of the formula I, i.e. the proportion of these compounds is ≧18%, preferably ≧25%, particularly preferably ≧35%.

The threshold voltages V$_{10/0/20}$ achieved are generally ≦1.8 volts, preferably ≦1.6 volts and particularly preferably in the range from 1.4 to 1.6 volts, or lower.

The mixtures according to the invention preferably contain fluorophenylcyclohexene derivatives of the subformulae I1 to I7:

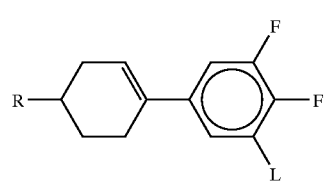

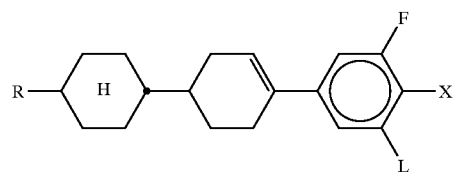

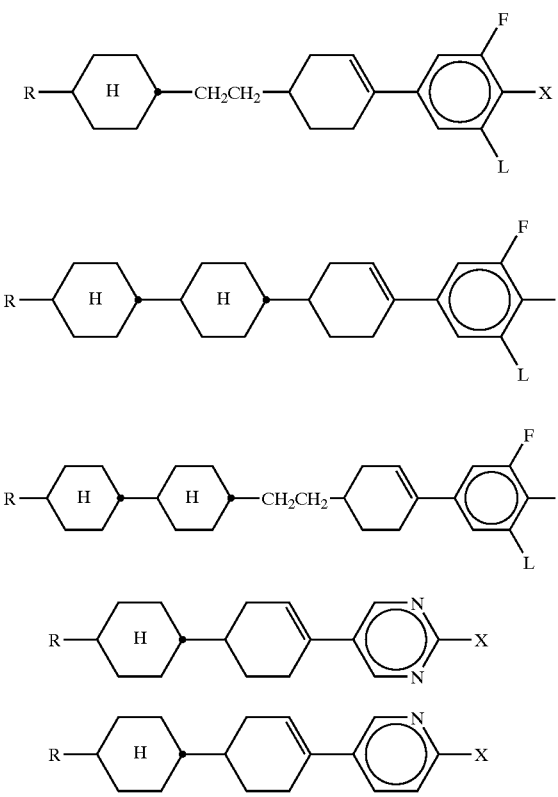

Of these, the compounds of the formula I2 are particularly preferred.

Particular preference is given to mixtures in which the radical X in the compounds of the formula I has the following meaning: F, Cl, OCF$_3$, OCHF$_2$, CF=CHF, OCH$_2$F, OCF$_2$Cl, OCFCl$_2$, CF$_3$, CF$_2$H, CH$_2$F, CF$_2$Cl, OCH$_2$CF$_3$, OCH$_2$CF$_2$H, CF=CF$_2$, CH=CF$_2$, CH=CHF, —O—CH=CF$_2$, —O—CH=CFCl, —OCH=CHF, in particular —CF=CF$_2$, —CH=CF$_2$, CN, F, Cl, OCF$_3$, OCHF$_2$OCH$_2$CF$_3$ or OCF=CF$_2$.

n is 0, 1 or 2, preferably 1. m is preferably 0.

If R is an alkyl radical, this can be straight-chain or branched. It is preferably straight-chain, has 2, 3, 4, 5, 6 or 7 carbon atoms and accordingly is preferably ethyl, propyl, butyl, pentyl, hexyl or heptyl, furthermore methyl, octyl, nonyl, decyl, undecyl, dodecyl, tridecyl, tetradecyl or pentadecyl.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 5-, 6-, 7- or 8-oxanonyl, or 2-, 3-, 4-, 5-, 6-, 7-, 8- or 9-oxadecyl.

If R is an alkenyl radical, this can be straight-chain or branched. It is preferably straight-chain and has 2 to 10 carbon atoms. Accordingly, it is in particular vinyl, prop-1- or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, or dec-1-, 2-, 3-, 4-, 5-, 6-, 7-, 8- or dec-9-enyl.

If R is an alkyl radical in which one CH$_2$ group has been replaced by —O— and one has been replaced by —CO—, these are preferably adjacent. These thus contain an acyloxy group —CO—O— or an oxycarbonyl group —O—CO—. These are preferably straight-chain and have 2 to 6 carbon atoms. Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If R is an alkenyl radical in which one CH$_2$ group has been replaced by CO or CO—O or O—CO—, this can be straight-chain or branched. It is preferably straight-chain and has 4 to 13 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

Compounds of the formula I which contain wing groups R which are suitable for polymerization reactions are suitable for the formation of liquid-crystalline polymers.

Compounds of the formula I containing branched wing groups R may occasionally be of importance due to better solubility in the customary liquid-crystalline base materials, but in particular as chiral dopes if they are optically active. Smectic compounds of this type are suitable as components of ferroelectric materials.

Branched groups of this type generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl, 4-methylhexyl, 2-nonyl, 2-decyl, 2-dodecyl, 6-methyloctoxy, 6-methyloctanoyloxy, 5-methylheptyloxycarbonyl, 2-methylbutyryloxy, 3-methylvaleryloxy, 4-methylhexanoyloxy, 2-chloropropionyloxy, 2-chloro-3-methylbutyryloxy, 2-chloro-4-methylvaleryloxy, 2-chloro-3-methylvaleryloxy, 2-methyl-3-oxapentyl and 2-methyl-3-oxahexyl.

Compounds of the formula I having $S_A$ phases are suitable, for example, for thermally addressed displays.

If R is an alkyl radical in which two or more $CH_2$ groups have been replaced by —O— and/or —CO—O—, this may be straight-chain or branched. It is preferably branched and has 3 to 12 carbon atoms. Accordingly, it is in particular biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl, 3,3-bis(ethoxycarbonyl)propyl, 4,4-bis(ethoxycarbonyl)butyl or 5,5-bis(ethoxycarbonyl)hexyl.

Compounds of the formula I which contain wing groups R which are suitable for polycondensations are suitable for the preparation of liquid-crystalline polycondensates.

The formula I covers both the racemates of these compounds and the optical antipodes, and mixtures thereof.

Of these compounds of the formula I and of the subformulae, preference is given to those in which at least one of the radicals present therein has one of the preferred meanings indicated.

In the compounds of the formula I, preferred stereoisomers are those in which the cyclohexane ring is trans-1,4-disubstituted.

The invention furthermore relates to the cyclohexene derivatives of the formulae I3, I6 and I7.

The invention furthermore relates to fluorophenylcyclohexene derivatives of the formulae in which R and m are as defined in claim 1, L is H or F and X is Q—Y, where Y is H, F or Cl and Q is —CHF—, —OCF$_2$—, —OCHF—, —OCH$_2$CF$_2$—, —CH═CF—, —CF═CF—, —CF═CH—, —O—CF═CF— or —OCH═CF—.

Particular preference is given to compounds in which m is 1.

The compounds of the formula I are prepared by methods known per se, as described in the literature (for example in the standard works, such as Houben-Weyl, Methoden der Organischen Chemie, Georg-Thieme-Verlag, Stuttgart), to be precise under reaction conditions which are known and are suitable for said reactions. Use may also be made here of variants which are known per se, but are not mentioned here in greater detail.

The fluorophenylcyclohexene derivatives of the formula I can be prepared, for example, as follows:

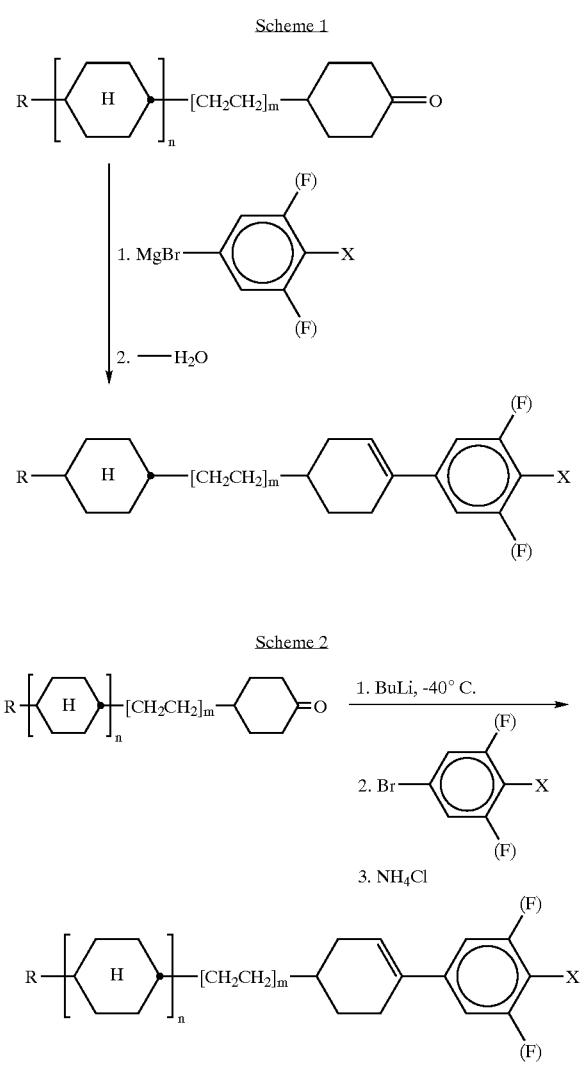

Scheme 3

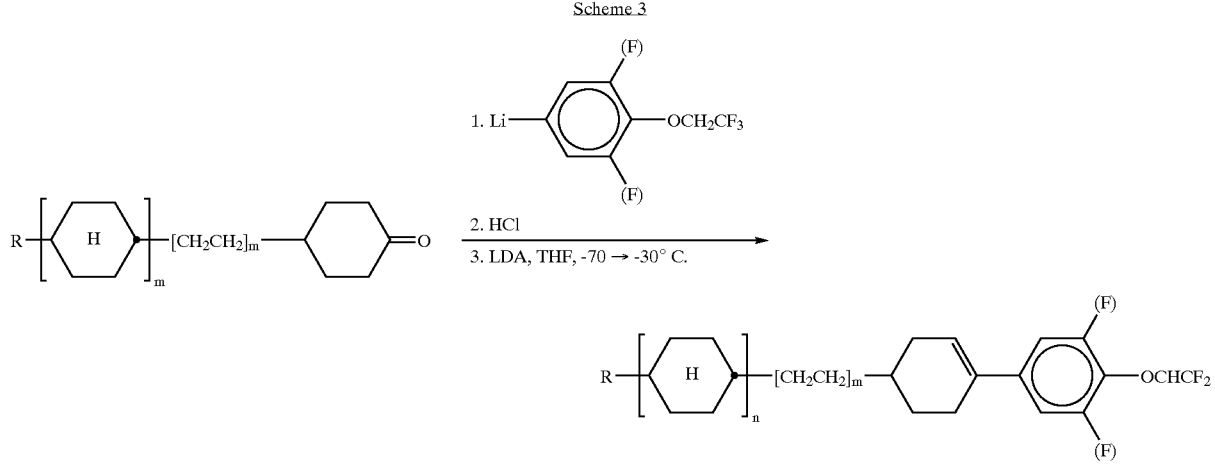

Preferred embodiments of the liquid-crystalline media according to the invention are given below:

The medium additionally contains one or more compounds selected from the group consisting of the general formulae II, III and IV:

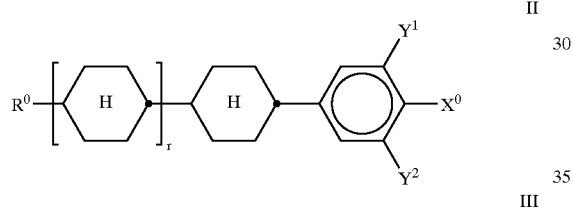

II

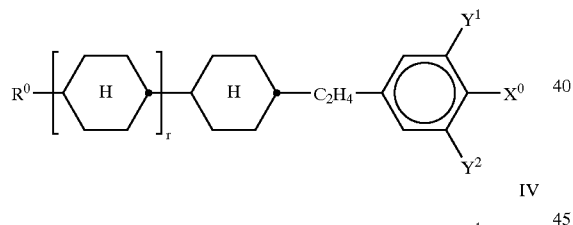

III

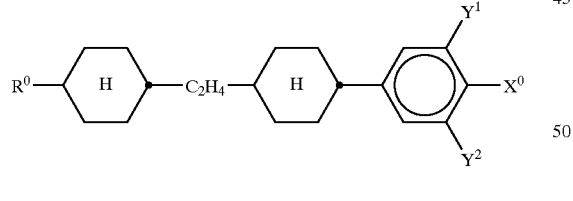

IV

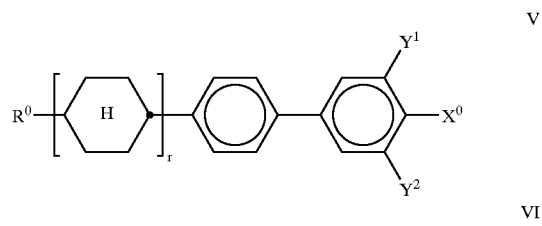

V

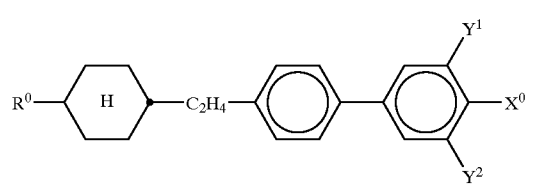

VI

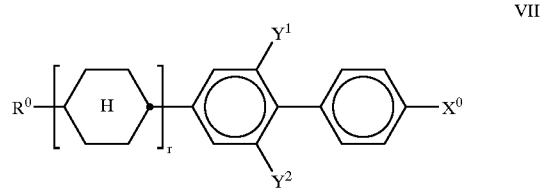

VII

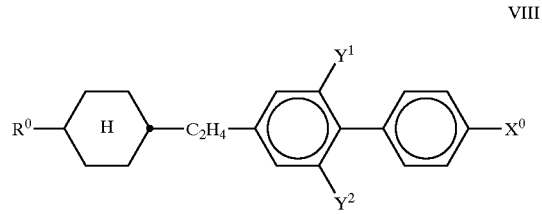

VIII in which the individual radicals have the following meanings:

$R^0$: alkyl, oxaalkyl, fluoroalkyl or alkenyl, in each case having up to 7 carbon atoms, $X^0$: F, Cl, $CF_3$, $OCF_3$, $OCHF_2$ or CN, $Y^2$ and $Y^2$ each H or F, r: 0 or 1.

The medium additionally contains one or more compounds selected from the group consisting of the general formulae V to VIII:

in which $R^0$: alkyl, oxaalkyl, fluoroalkyl or alkenyl, in each case having up to 7 carbon atoms, $X^0$: F, Cl, $CF_3$, $OCF_3$, $OCHF_2$ or CN, $Y^2$ and $Y^2$: each, independently of one another, H or F, and r: 0 or 1.

The medium additionally contains one or more compounds selected from the group consisting of the general formulae IX to XII:

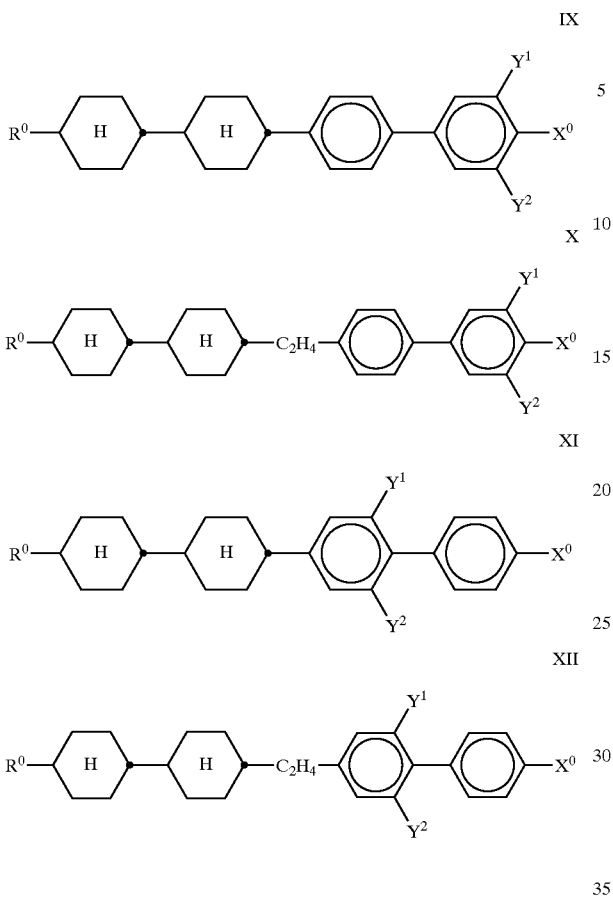

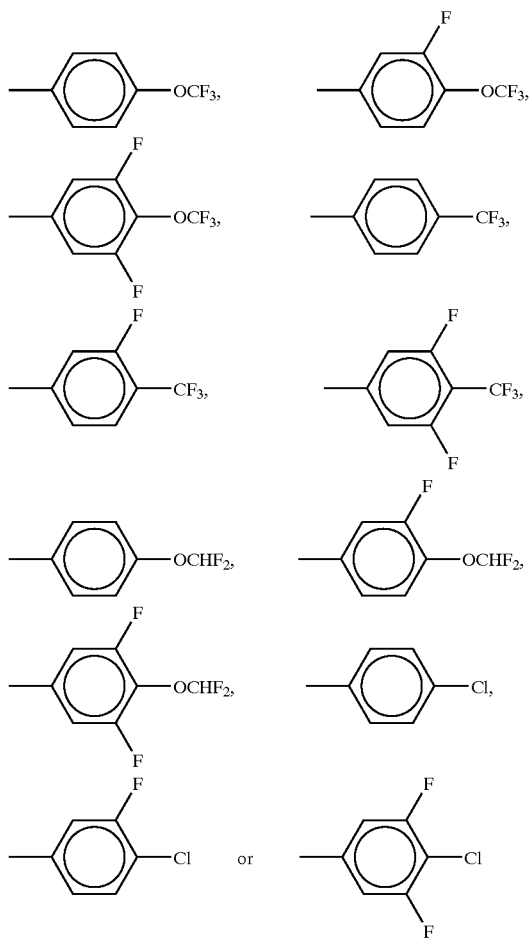

in which $R^0$, $X^0$, $Y^1$ and $Y^2$ each, independently of one another, have one of the meanings given for V–VIII above.

The proportion of compounds of the formulae I to IV together in the total mixture is at least 50% by weight.

The proportion of compounds of the formula I in the total mixture is from 10 to 50% by weight.

The proportion of compounds of the formulae II to IV in the total mixture is from 30 to 70% by weight.

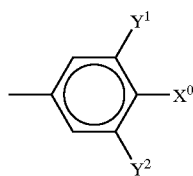

is preferably

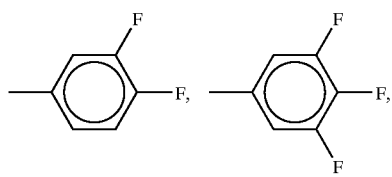

The medium contains compounds of the formulae II and III or IV.

$R^0$ is straight-chain alkyl or alkenyl having 2 to 7 carbon atoms.

The medium essentially comprises compounds of the formulae I to IV.

The medium contains further compounds, preferably selected from the following group consisting of the general formulae XIII to XV:

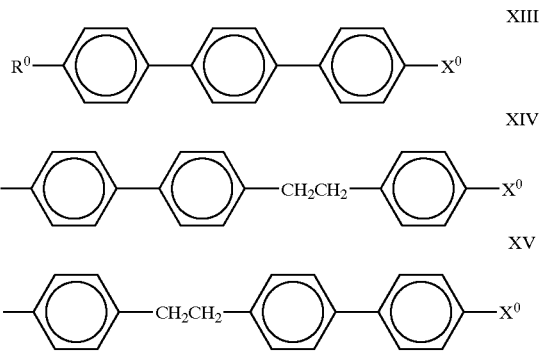

in which $R^0$ and $X^0$ are as defined as for V–VIII, above, the 1,4-phenylene rings may be substituted by CN, chlorine or fluorine.

The weight ratio I: (II+III+IV) is preferably from 1:10 to 1:1.

The medium essentially comprises compounds selected from the group consisting of the general formulae I to XV.

It has been found that even a relatively small proportion of compounds of the formula I mixed with conventional liquid-crystal materials, but in particular with one or more compounds of the formula II, III and/or IV, results in a significant increase in the pitch angle and in low values for the birefringence, and at the same time broad nematic phases with low smectic-nematic transition temperatures are observed. The compounds of the formulae I to IV are colorless stable and readily miscible with one another and with other liquid-crystal materials.

The term "alkyl" includes straight-chain and branched alkyl groups having 1–7 carbon atoms, in particular the straight-chain groups methyl, ethyl, propyl, butyl, pentyl, hexyl and heptyl. Group [sic] having 2–5 carbon atoms are generally preferred.

The term "alkenyl" includes straight-chain and branched alkenyl groups having 2–7 carbon atoms, in particular the straight-chain groups. Particularly [sic] alkenyl groups are $C_2$–$C_7$-1E-alkenyl, $C_4$–$C_7$-3E-alkenyl, $C_5$–$C_7$-4-alkenyl, $C_6$–$C_7$-5-alkenyl and $C_7$-6-alkenyl, in particular $C_2$–$C_7$-1E-alkenyl, $C_4$–$C_7$-3E-alkenyl and $C_5$–$C_7$-4-alkenyl. Examples of preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" preferably includes straight-chain groups containing terminal fluorine, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "oxaalkyl" preferably includes straight-chain radicals of the formula $C_nH_{2n+1}$—O—$(CH_2)_m$ in which n and m are each, independently of one another, 1 to 6. n is preferably 1 and m is preferably 1 to 6.

Through a suitable choice of the meanings of $R^0$ and $X_0$, the addressing times, the threshold voltage, the gradient of the transmission characteristic lines, etc., can be modified as desired. For example, 1E-alkenyl radicals, 3E-alkenyl radicals, 2E-alkenyloxy radicals and the like generally give shorter addressing times, improved nematic tendencies and a higher ratio between the elastic constants $k_{33}$ (bend) and $k_{11}$ (splay) compared with alkyl and alkoxy radicals. 4-Alkenyl radicals, 3-alkenyl radicals and the like generally give lower threshold voltages and lower values of $k_{33}/k_{11}$ compared with alkyl and alkoxy radicals.

A —$CH_2CH_2$— group in $Z^1$ or $Z^2$ generally results in higher values of $k_{33}/k_{11}$ compared with a single covalent bond. Higher values of $k_{33}/k_{11}$ facilitate, for example, flatter transmission characteristic lines in TN cells with a 90° twist (for achieving gray tones) and steeper transmission characteristic lines in STN, SBE and OMI cells (greater multiplexing ability), and vice versa.

The optimum mixing ratio of the compounds of the formulae I and II+III+IV depends substantially on the desired properties, on the choice of the components of the formulae I, II, III and/or IV and on the choice of any other components which may be present. Suitable mixing ratios within the abovementioned range can easily be determined from case to case.

The total amount of compounds of the formulae I to XV in the mixtures according to the invention is not crucial. The mixtures may therefore contain one or more further components in order to optimize various properties. However, the observed effect on the addressing times and the threshold voltage is generally greater the higher the total concentration of compounds of the formulae I to XV.

In a particularly preferred embodiment, the media according to the invention contain compounds of the formula II, III, V and/or VII (preferably II and/or III) in which $X^0$ is $CF_3$, $OCF_3$ or $OCHF_2$. A favorable synergistic effect with the compounds of the formula I results in particularly advantageous properties.

For STN applications, the media preferably contain compounds selected from the group consisting of the formulae V to VIII in which $X^0$ is preferably $OCHF_2$ or CN.

The media according to the invention may furthermore contain a component A comprising one or more compounds of the general formula I' having a dielectric anisotropy of from –1.5 to +1.5

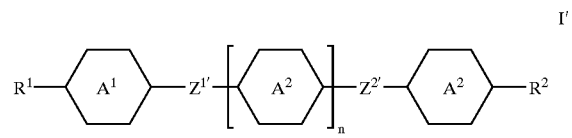

in which

R¹ and R² are each, independently of one another, n-alkyl, n-alkoxy, ω-fluoroalkyl or n-alkenyl having up to 9 carbon atoms,

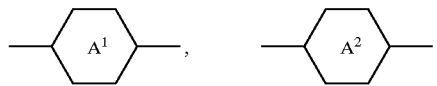

and

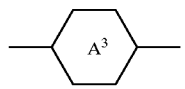

are each, independently of one another, 1,4-phenylene, 2- or 3-fluoro-1,4-phenylene, trans-1,4-cyclohexylene or 1,4-cyclohexenylene, $Z^1$ and $Z^2$ are each, independently of one another, —$CH_2CH_2$—, —C≡C—, —CO—O—, —O—CO—, or a single bond, and n is 0, 1 or 2.

Component A preferably contains one or more compounds selected from the group consisting of II1 to II7:

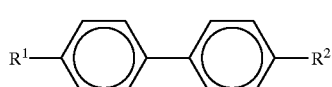

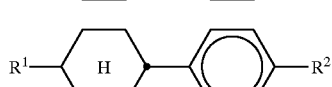

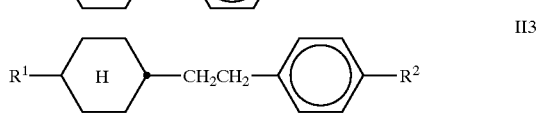

-continued

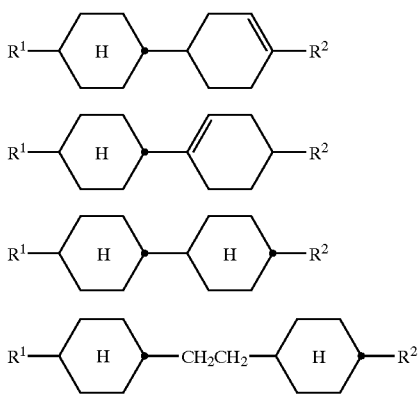

in which $R^1$ and $R^2$ are as defined under the formula I'.

Component A preferably additionally contains one or more compounds selected from the group consisting of II8 to II20:

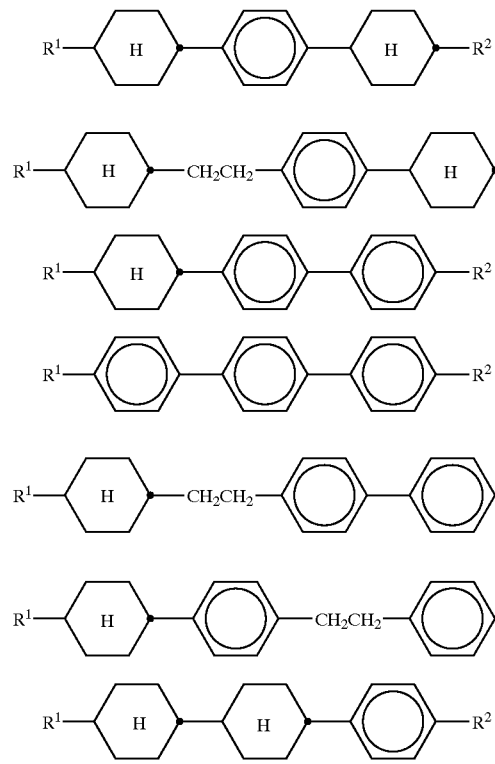

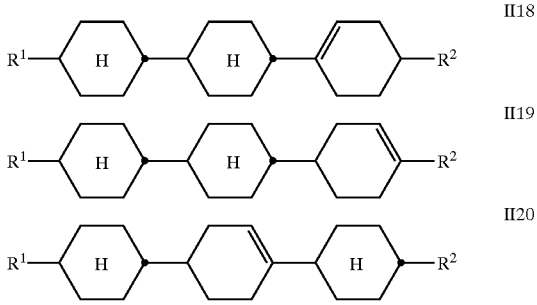

in which $R^1$ and $R^2$ are as defined under the formula I', and the 1,4-phenylene groups in II8 to II17 may each, independently of one another, also be monosubstituted or polysubstituted by fluorine.

Furthermore, component A preferably additionally contains one or more compounds selected from the group consisting of II21 to II25:

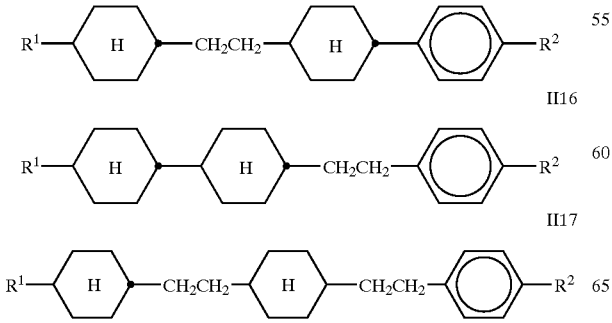

in which $R^1$ and $R^2$ are as defined under the formula I' and the 1,4-phenylene groups in II21 to II25 may each, independently of one another, also be monosubstituted or polysubstituted by fluorine.

Finally, preferred mixtures of this type are those in which component A contains one or more compounds selected from the group consisting of II26 and II27:

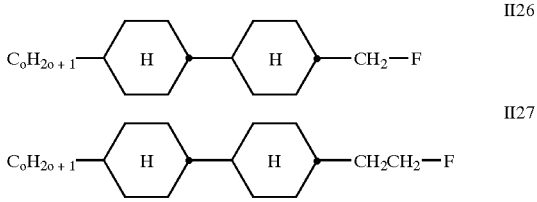

in which $C_oH_{2o+1}$ is a straight-chain alkyl group having up to 7 carbon atoms.

In some cases, the addition of compounds of the formula

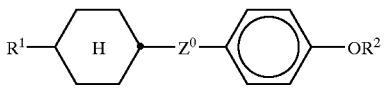

in which

R$^1$ and R$^2$ are as defined under the formula I'
and
Z$^0$ is a single bond, —CH$_2$CH$_2$—,

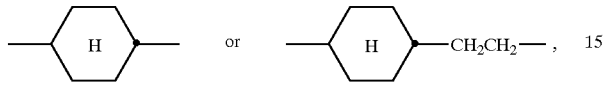

proves advantageous for suppressing smectic phases, although this may reduce the specific resistance. In order to achieve parameter combinations which are ideal for the application, a person skilled in the art can easily determine whether and, if yes, in what amount these compounds may be added. Normally, less than 15%, in particular 5–10%, are used.

Preference is given to liquid-crystal mixtures which contain one or more compounds selected from the group consisting of Ia to Id:

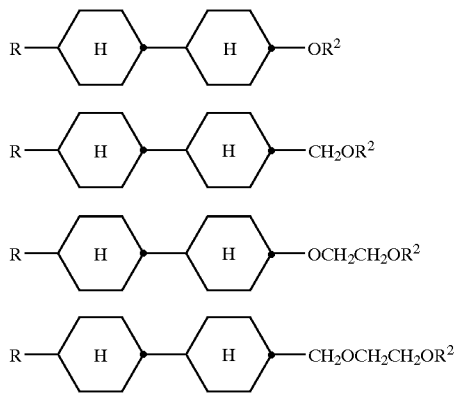

in which R$^2$ is n-alkyl having up to 5 carbon atoms.

The type and amount of the polar compounds having positive dielectric anisotropy are not crucial per se. A person skilled in the art can use simple routine experiments to select suitable materials from a wide range of known and, in many cases, also commercially available components and base mixtures. The media according to the invention preferably contain one or more compounds of the formula I"

I"

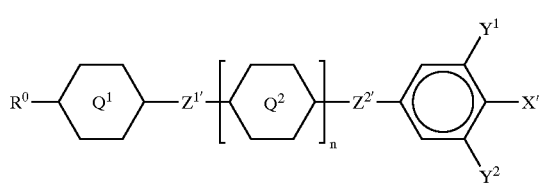

in which Z$^{1'}$, Z$^{2'}$ and n are as defined under the formula I',

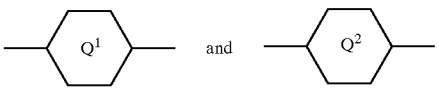

are each, independently of one another, 1,4-phenylene, trans-1,4-cyclohexylene or 3-fluoro-1,4-phenylene, or one of the radicals

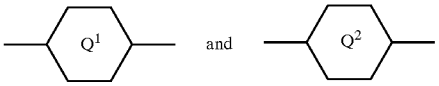

is alternatively trans-1,3-dioxane-2,5-diyl, pyrimidine-2,5-diyl, pyridine-2,5-diyl or 1,4-cyclohexenylene, R$^0$ is n-alkyl, n-alkenyl, n-alkoxy or n-oxaalkyl, in each case having up to 9 carbon atoms, Y$^1$ and Y$^2$ are each, independently of one another, H or F and X' is CN, halogen, CF$_3$, OCF$_3$ or OCHF$_2$.

In a preferred embodiment, the media according to the invention for STN or TN applications are based on compounds of the formula I" in which X' is CN. It goes without saying that smaller or larger proportions of other compounds of the formula I" (X'≠CN) are also possible. For MLC applications, the media according to the invention preferably contain only up to about 10% of nitriles of the formula I" (but preferably no nitriles of the formula I", but instead compounds of the formula I' where X' is halogen, CF$_3$, OCF$_3$ or OCHF$_2$). These media are preferably based on the compounds of the formulae II to XV.

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-biscyclohexylbenzenes, 4,4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

| | |
|---|---|
| R'-L-E-R" | 1 |
| R'-L-COO-E-R" | 2 |
| R'-L-OOC-E-R" | 3 |
| R'-L-CH$_2$CH$_2$-E-R" | 4 |
| R'-L-C≡C-E-R" | 5 |

In the formulae 1, 2, 3, 4 and 5, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group comprising -Phe-Cyc-, -Cyc-Cyc-, -G-Phe- and -G-Cyc-.

In a smaller sub-group of the compounds of the formulae 1, 2, 3, 4 and 5, R' and R" are in each case, independently of one another, alkyl, alkenyl, alkoxy, alkoxyalkyl, alkenyloxy or alkanoyloxy having up to 8 carbon atoms. This smaller sub-group is called group A below, and the compounds are labelled with the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5 which is known as group B, R" is —F, —Cl, —NCS or —(O)$_i$CH$_{3-(k+1)}$F$_k$Cl$_l$, where i is 0 or 1, and k+l is 1, 2 or 3; the compounds in which R" has this meaning are labelled with the sub-formulae 1b, 2b, 3b, 4b and 5b. Particular preference is given to those compounds of the sub-formulae 1b, 2b, 3b, 4b and 5b in which R" is —F, —Cl, —NCS, —CF$_3$, —OCHF$_2$ or —OCF$_3$.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and 5, R" is —CN; this sub-group is known as group C below, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a–5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides compounds of the formula I according to the invention, the media according to the invention preferably contain one or more compounds selected from group A and/or group B and/or group C. The proportions by weight of the compounds from these groups in the media according to the invention are preferably Group A: 0 to 90%, preferably 20 to 90%, in particular 30 to 90%

Group B: 0 to 80%, preferably 10 to 80%, in particular 10 to 65%

Group C: 0 to 80%, preferably 5 to 80%, in particular 5 to 50%, the sum of the proportions by weight of the group A and/or B and/or C compounds present in the particular media according to the invention preferably being 5% to 90% and in particular 10% to 90%.

The media according to the invention preferably contain 1 to 40%, particularly preferably 5 to 30%, of compounds according to the invention. Further preferred media are those which contain more than 40%, in particular 45 to 90%, of compounds according to the invention. The media preferably contain three, four or five compounds according to the invention.

The construction of the STN and MLC displays according to the invention from polarizers, electrode base plates and electrodes with surface treatment corresponds to the construction which is conventional for displays of this type. The term conventional construction here is widely drawn and also covers all derivatives and modifications of the MLC display, in particular also matrix display elements based on poly-Si TFTs or MIMs.

An essential difference between the displays according to the invention and those customary hitherto based on the twisted nematic cell is, however, the choice of liquid-crystal parameters in the liquid-crystal layer.

The liquid-crystal mixtures which can be used according to the invention are prepared in a manner which is conventional per se. In general, the desired amount of the components used in a lesser amount is dissolved in the components making up the principal constituent, expediently at elevated temperature. It is also possible to mix solutions of the components in an organic solvent, for example acetone, chloroform or methanol, and, after thorough mixing, to remove the solvent again, for example by distillation.

The dielectrics may also contain other additives known to those skilled in the art and described in the literature. For example, 0–15% of pleochroic dyes or chiral dopes can be added.

In the following discussion, C denotes a crystalline phase, S a smectic phase, S$_B$ a smectic B phase, N a nematic phase and I the isotropic phase.

V$_{10}$ denotes the voltage for 10% transmission (viewing direction perpendicular to the plate surface). t$_{on}$ denotes the switch-on time and t$_{off}$ the switch-off time at an operating voltage corresponding to 2.5 times the value of V$_{10}$. An denotes the optical anisotropy and no the refractive index. Δε denotes the dielectric anisotropy (Δε=ε$_∥$-ε$_⊥$, where ε$_∥$ is the dielectric constant parallel to the longitudinal molecular axes and ε$_⊥$ is the dielectric constant perpendicular thereto. The electro-optical data were measured in a TN cell in the 1st minimum (i.e. at a d Δn value of 0.5 mm) at 20° C., unless expressly stated otherwise. The optical data were measured at 20° C., unless expressly stated otherwise.

In the present application and in the examples below, the structures of the liquid-crystal compounds are indicated by acronyms, with the transformation into chemical formulae taking place in accordance with Tables A and B below. All radicals $C_nH_{2n+1}$ are straight-chain alkyl radicals containing n carbon atoms. The coding in Table B is self-evident. In Table A, only the acronym for the base structure is given. In individual cases, the acronym for the base structure is followed, separated by a hyphen, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | F | H |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | F | H |
| nCF$_3$ | $C_nH_{2n+1}$ | CF$_3$ | H | H |
| nOCF$_3$ | $C_nH_{2n+1}$ | OCF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |
| nS | $C_nH_{2n+1}$ | NCS | H | H |
| rVsN | $C_rH_{2r+1}-CH=CH-C_2H_{2s}-$ | CN | H | H |
| rEsN | $C_rH_{2r+1}-O-C_2H_{2s}-$ | CN | H | H |
| nAm | $C_nH_{2n+1}$ | COCC$_m$H$_{2m+1}$ | H | H |
| nF.F.F | $C_nH_{2n+1}$ | F | F | F |
| nCl.F.F | $C_nH_{2n+1}$ | Cl | F | F |
| nCF$_3$.F.F | $C_nH_{2n+1}$ | CF$_3$ | F | F |
| nOCF$_3$.F.F | $C_nH_{2n+1}$ | OCF$_3$ | F | F |
| nOCF$_2$.F.F | $C_nH_{2n+1}$ | OCHF$_2$ | F | F |
| nOCF$_3$.F | $C_nH_{2n+1}$ | OCF$_3$ | F | H |

TABLE A

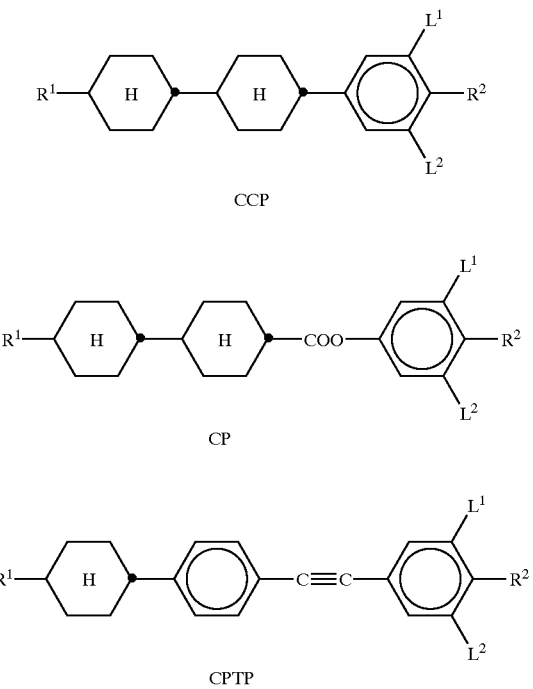

PYP

PYRP

BCH

CBC

TABLE A-continued

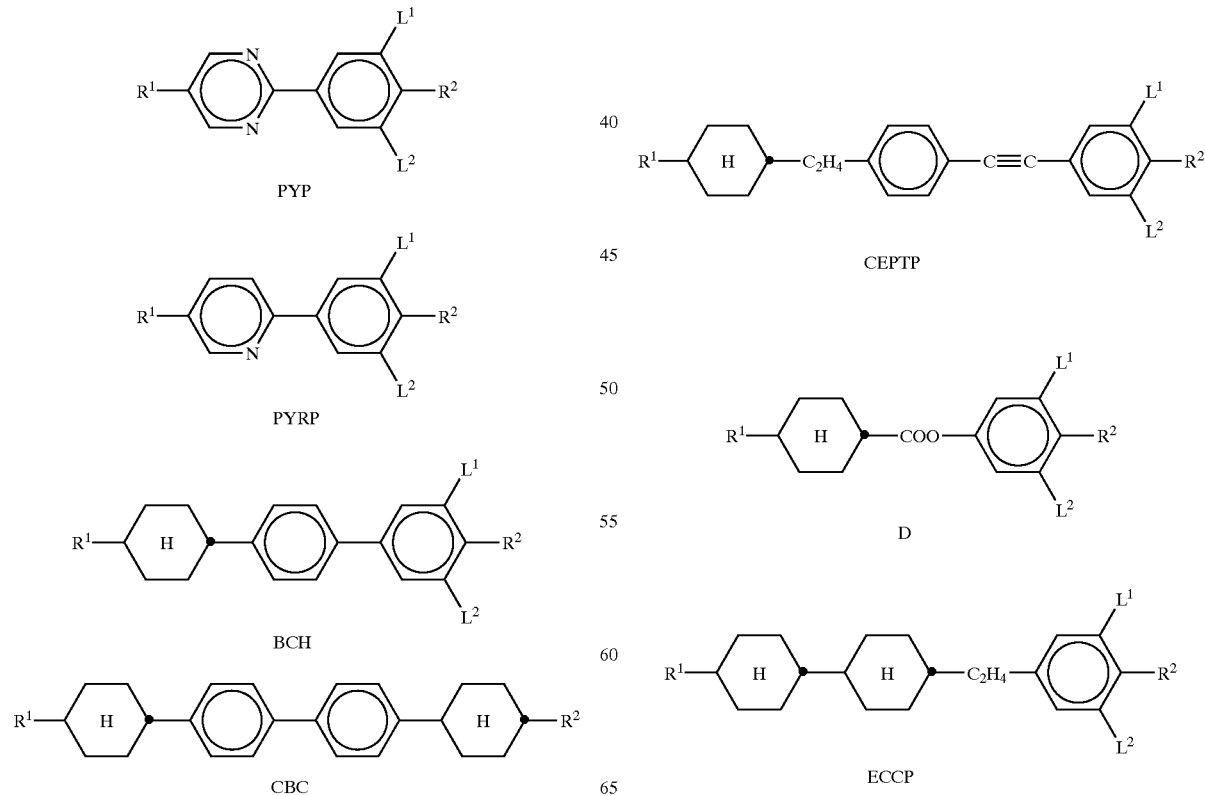

CCH

CCP

CP

CPTP

CEPTP

D

ECCP

TABLE A-continued
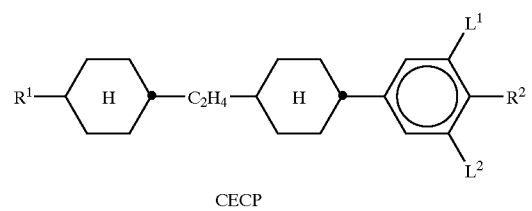
CECP
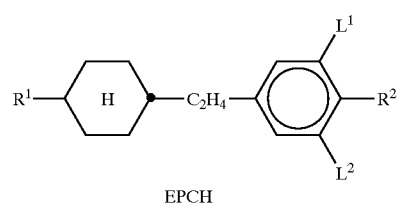
EPCH
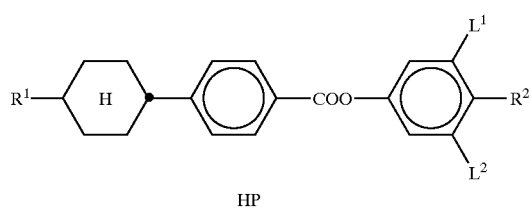
HP
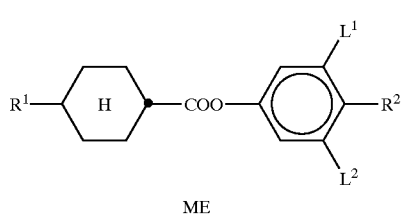
ME
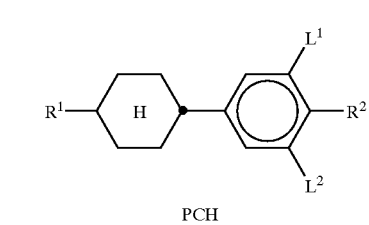
PCH
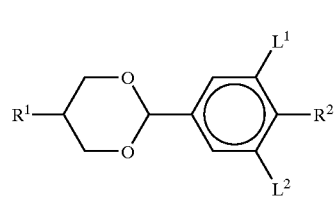
PDX
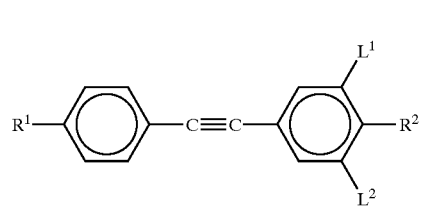
PTP
TABLE A-continued
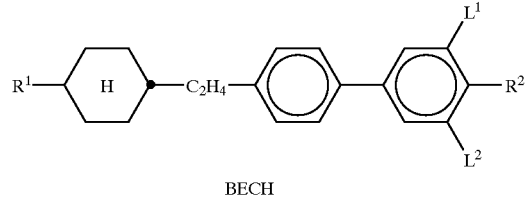
BECH
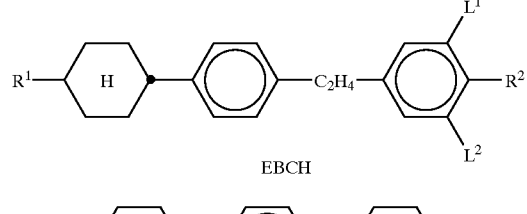
EBCH
CPC
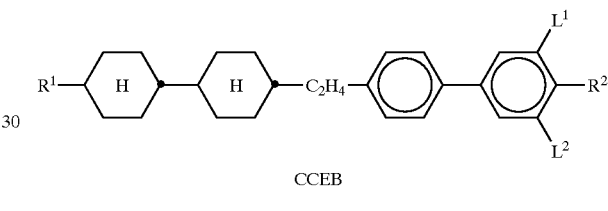
CCEB
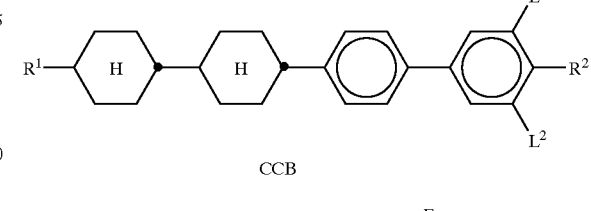
CCB
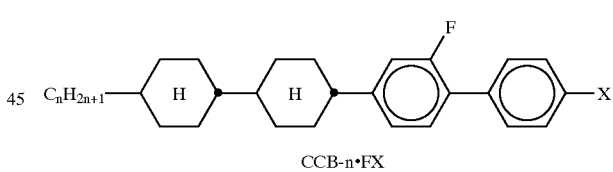
CCB-n·FX
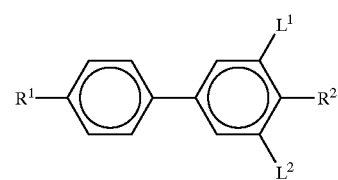
B
TABLE B
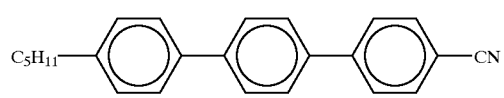
T15

TABLE B-continued

K3n, M3n, BCH-n·FX, Inm, CBC-nmF, CCPC-nm, CHE, ECBC-nm, ECCH-nm, CCH-n1EM, CUP-nX, T-nFN, CCUP-nX, CCECP-nX·F, CCP-nF·F·F, CUP-nX·F, BCH-nF·F·F, CLU-nX

TABLE B-continued

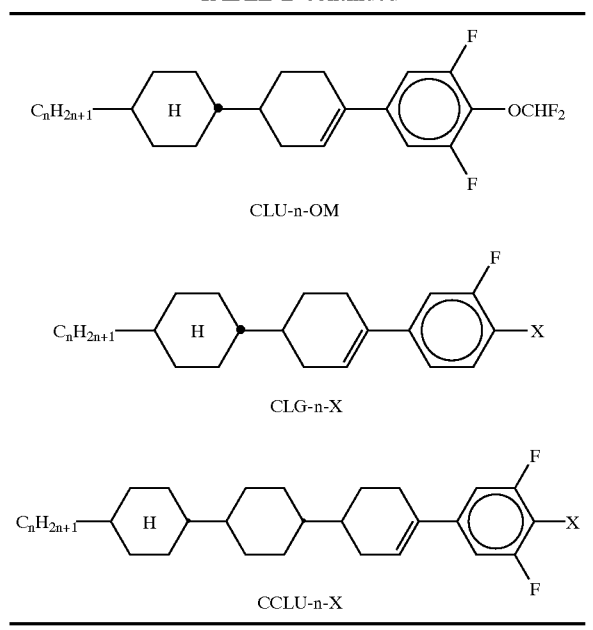

"Conventional work-up" means that water is added, the mixture is extracted with dichloromethane, the phases are separated, the organic phase is dried and evaporated, and the product is purified by crystallization and/or chromatography.

In addition, the abbreviations have the following meanings:

K: crystalline solid state, S: smectic phase (the index denotes the phase type), N: nematic state, Ch: cholesteric phase, I: isotropic phase. The number between two symbols indicates the transition temperature in degrees celsius.

| DAST | diethylaminosulfur trifluoride |
| DCC | dicyclohexylcarbodiimide |
| DDQ | dichlorodicyanobenzoquinone |
| DIBALH | diisobutylaluminum hydride |
| DMSO | dimethyl sulfoxide |
| POT | potassium tert-butoxide |
| THF | tetrahydrofuran |
| pTsOH | p-toluene sulfonic acid |

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding applications German P 43 11 780.5, filed Apr. 9, 1993 and German P 43 12 968.4, filed Apr. 21, 1993, are hereby incorporated by reference.

EXAMPLES

Example 1 a)

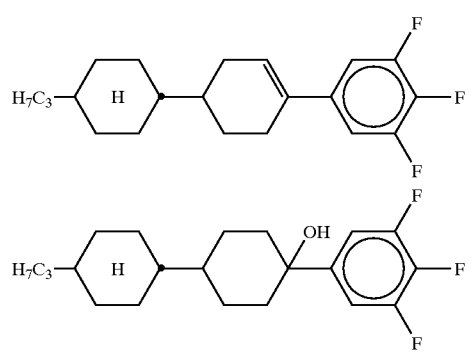

170 mmol of 3,4,5-trifluorobromobenzene are dissolved in 350 ml of diethyl ether and cooled to −70° C. with stirring. 170 mmol of n-BuLi are added dropwise to the cooled solution. The mixture is stirred for a further 0.5 hour, and trans-4-[trans-4-propylcyclohexyl]cyclohexanone in 50 ml of diethyl ether is then added dropwise to the solution cooled to −70° C. The reaction mixture is allowed to warm to room temperature, water is added, and the mixture is acidified by means of dilute HCl. The mixture is subsequently extracted with methyl t-butyl ether and subjected to customary work-up.

b)

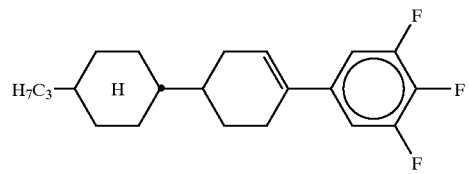

170 mmol of the crude product from Example 1a) are dissolved in 300 ml of toluene and refluxed for 2 hours on a water separator together with 3 g of p-toluenesulfonic acid. The mixture is subsequently washed with water until neutral, the solvent is removed, and the mixture is subjected to customary work-up. C 62 N 80.5 I; Δε=10.79; Δn=+0.105

The following compounds of the formula

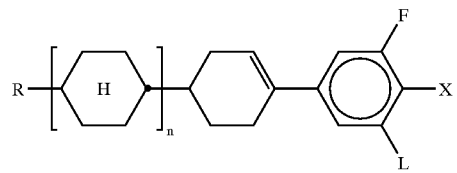

are prepared analogously:

| R | n | X | L | |
|---|---|---|---|---|
| H | 1 | F | F | C 54 I; Δε = 7.96; Δn = +0.050 |
| C$_2$H$_5$ | 1 | F | F | C 59 I; Δε = 10.81; Δn = +0.092 |
| n-C$_4$H$_9$ | 1 | F | F | |

-continued

| R | n | X | L | |
|---|---|---|---|---|
| n-C$_5$H$_{11}$ | 1 | F | F | C 68 N 93.8 I; Δε = 9.3; Δn = +0.100 |
| n-C$_6$H$_{13}$ | 1 | F | F | |
| C$_2$H$_5$ | 1 | Cl | F | |
| n-C$_3$H$_7$ | 1 | Cl | F | |
| n-C$_4$H$_9$ | 1 | Cl | F | |
| n-C$_5$H$_{11}$ | 1 | Cl | F | |
| n-C$_6$H$_{13}$ | 1 | Cl | F | |
| n-C$_7$H$_{15}$ | 1 | Cl | F | |
| C$_2$H$_5$ | 0 | F | F | |
| n-C$_3$H$_7$ | 0 | F | F | |
| n-C$_4$H$_9$ | 0 | F | F | |
| n-C$_5$H$_{11}$ | 0 | F | F | |
| n-C$_6$H$_{13}$ | 0 | F | F | |
| C$_2$H$_5$ | 0 | Cl | F | |
| n-C$_3$H$_7$ | 0 | Cl | F | |
| n-C$_4$H$_9$ | 0 | Cl | F | |
| n-C$_5$H$_{11}$ | 0 | Cl | F | |
| n-C$_6$H$_{13}$ | 0 | Cl | F | |
| C$_2$H$_5$ | 2 | F | F | |
| n-C$_3$H$_7$ | 2 | F | F | C 109 N 246.2 I; Δε =10.4; Δn = +0.111 |
| n-C$_4$H$_9$ | 2 | F | F | |
| n-C$_5$H$_{11}$ | 2 | F | F | |
| n-C$_6$H$_{13}$ | 2 | F | F | |
| C$_2$H$_5$ | 2 | Cl | F | |
| n-C$_3$H$_7$ | 2 | Cl | F | |
| n-C$_4$H$_9$ | 2 | Cl | F | |
| n-C$_5$H$_{11}$ | 2 | Cl | F | |
| n-C$_6$H$_{13}$ | 2 | Cl | F | |
| H | 1 | F | H | |
| C$_2$H$_5$ | 1 | F | H | |
| n-C$_3$H$_7$ | 1 | F | H | C 45 N 115.6 I; Δn = +0.115; Δε = 6.9 |
| n-C$_5$H$_{11}$ | 1 | F | H | |
| n-C$_6$H$_{13}$ | 1 | F | H | |
| C$_2$H$_5$ | 1 | Cl | H | |
| n-C$_3$H$_7$ | 1 | Cl | H | |
| n-C$_5$H$_{11}$ | 1 | Cl | H | |
| n-C$_6$H$_{13}$ | 1 | Cl | H | |

Example 2

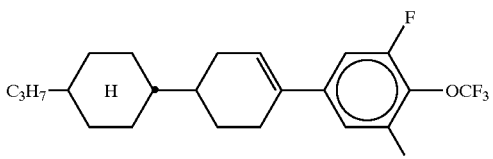

0.08 mol of 2,6-difluoro-4-bromotrifluoromethoxybenzene are dissolved in 100 ml of diethyl ether, and 0.08 mol of n-BuLi is added at from −30 to −40° C. The mixture is stirred for a further 15 minutes, and 0.08 mol of trans-4-[trans-4-propylcyclohexyl]cyclohexanone in 30 ml of diethyl ether is then added dropwise at from −25 to −20° C. The mixture is stirred for a further one hour without cooling, during which the solution warms to room temperature. The product is hydrolyzed by means of saturated ammonium chloride solution, the mixture is acidified by means of 10% hydrochloric acid, and the organic phase is separated off and then subjected to customary work-up. The product is dissolved in 120 ml of toluene, 3 g of p-toluenesulfonic acid are added, and the mixture is boiled for 1 hour on a water separator. The reaction mixture is then washed with water and saturated sodium chloride solution and subjected to customary work-up.

The following compounds of the formula

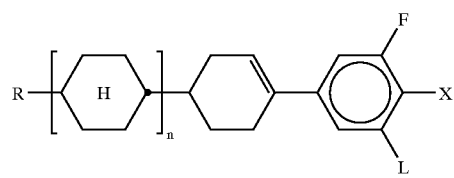

are prepared analogously. The temperature for the halometallation should be chosen at between −100 and −30° C., depending on X.

| R | n | X | L |
|---|---|---|---|
| C$_2$H$_5$ | 1 | OCF$_3$ | H |
| C$_2$H$_5$ | 1 | OCF$_3$ | F |
| n-C$_4$H$_9$ | 1 | OCF$_3$ | H |
| n-C$_4$H$_9$ | 1 | OCF$_3$ | F |
| n-C$_5$H$_{11}$ | 1 | OCF$_3$ | H |
| n-C$_5$H$_{11}$ | 1 | OCF$_3$ | F |
| n-C$_6$H$_{13}$ | 1 | OCF$_3$ | H |
| n-C$_6$H$_{13}$ | 1 | OCF$_3$ | F |
| n-C$_3$H$_7$ | 1 | CH=CF$_2$ | H |
| n-C$_3$H$_7$ | 1 | CH=CF$_2$ | F |
| n-C$_5$H$_{11}$ | 1 | CH=CF$_2$ | H |
| n-C$_5$H$_{11}$ | 1 | CH=CF$_2$ | F |
| n-C$_3$H$_7$ | 1 | CF=CF$_2$ | H |
| n-C$_3$H$_7$ | 1 | CF=CF$_2$ | F |
| n-C$_5$H$_{11}$ | 1 | CF=CF$_2$ | H |
| n-C$_5$H$_{11}$ | 1 | CF=CF$_2$ | F |
| n-C$_3$H$_7$ | 1 | CF=CHF | H |
| n-C$_3$H$_7$ | 1 | CF=CHF | F |
| n-C$_5$H$_{11}$ | 1 | CF=CHF | H |
| n-C$_5$H$_{11}$ | 1 | CF=CHF | F |
| C$_2$H$_5$ | 1 | OCHF$_2$ | H |
| C$_2$H$_5$ | 1 | OCHF$_2$ | F |
| n-C$_3$H$_7$ | 1 | OCHF$_2$ | H |
| n-C$_3$H$_7$ | 1 | OCHF$_2$ | F C54 N 113.9 I: Δn = +0.114; Δs = 11.11 |
| n-C$_4$H$_9$ | 1 | OCHF$_2$ | H |
| n-C$_4$H$_9$ | 1 | OCHF$_2$ | F |
| n-C$_5$H$_{11}$ | 1 | OCHF$_2$ | H |
| n-C$_5$H$_{11}$ | 1 | OCHF$_2$ | F |
| n-C$_6$H$_{13}$ | 1 | OCHF$_2$ | H |
| n-C$_6$H$_{13}$ | 1 | OCHF$_2$ | F |
| C$_2$H$_5$ | 1 | CF$_3$ | F |
| n-C$_3$H$_7$ | 1 | CF$_3$ | F |
| n-C$_4$H$_9$ | 1 | CF$_3$ | F |
| n-C$_5$H$_{11}$ | 1 | CF$_3$ | F |
| n-C$_6$H$_{13}$ | 1 | CF$_3$ | F |
| C$_2$H$_5$ | 1 | OCH$_2$F | H |
| C$_2$H$_5$ | 1 | OCH$_2$F | F |
| n-C$_3$H$_7$ | 1 | OCH$_2$F | H |
| n-C$_3$H$_7$ | 1 | OCH$_2$F | F |
| n-C$_5$H$_{11}$ | 1 | OCH$_2$F | H |
| n-C$_5$H$_{11}$ | 1 | OCH$_2$F | F |
| C$_2$H$_5$ | 1 | OCF$_2$Cl | H |
| C$_2$H$_5$ | 1 | OCF$_2$Cl | F |
| n-C$_3$H$_7$ | 1 | OCF$_2$Cl | H |
| n-C$_3$H$_7$ | 1 | OCF$_2$Cl | F |
| n-C$_5$H$_{11}$ | 1 | OCF$_2$Cl | H |
| n-C$_5$H$_{11}$ | 1 | OCF$_2$Cl | F |
| C$_2$H$_5$ | 1 | OCFCl$_2$ | H |
| C$_2$H$_5$ | 1 | OCFCl$_2$ | F |
| n-C$_3$H$_7$ | 1 | OCFCl$_2$ | H |
| n-C$_3$H$_7$ | 1 | OCFCl$_2$ | F |
| n-C$_5$H$_{11}$ | 1 | OCFCl$_2$ | H |
| n-C$_5$H$_{11}$ | 1 | OCFCl$_2$ | F |
| C$_2$H$_5$ | 1 | CF$_2$H | H |
| C$_2$H$_5$ | 1 | CF$_2$H | F |
| n-C$_3$H$_7$ | 1 | CF$_2$H | H |
| n-C$_3$H$_7$ | 1 | CF$_2$H | F |
| n-C$_5$H$_{11}$ | 1 | CF$_2$H | H |
| n-C$_5$H$_{11}$ | 1 | CF$_2$H | F |

| R | n | X | L |
|---|---|---|---|
| n-C₆H₁₃ | 1 | CF₂H | H |
| n-C₆H₁₃ | 1 | CF₂H | F |
| C₂H₅ | 1 | CH₂F | H |
| C₂H₅ | 1 | CH₂F | F |
| n-C₃H₇ | 1 | CH₂F | H |
| n-C₃H₇ | 1 | CH₂F | F |
| n-C₅H₁₁ | 1 | CH₂F | H |
| n-C₅H₁₁ | 1 | CH₂F | F |
| C₂H₅ | 1 | CF₂Cl | H |
| C₂H₅ | 1 | CF₂Cl | F |
| n-C₃H₇ | 1 | CF₂Cl | H |
| n-C₃H₇ | 1 | CF₂Cl | F |
| n-C₅H₁₁ | 1 | CF₂Cl | H |
| n-C₅H₁₁ | 1 | CF₂Cl | F |
| C₂H₅ | 1 | OCH₂CF₃ | H |
| C₂H₅ | 1 | OCH₂CF₃ | F |
| n-C₃H₇ | 1 | OCH₂CF₃ | H |
| n-C₃H₇ | 1 | OCH₂CF₃ | F |
| n-C₅H₁₁ | 1 | OCH₂CF₃ | H |
| n-C₅H₁₁ | 1 | OCH₂CF₃ | F |
| n-C₆H₁₃ | 1 | OCH₂CF₃ | H |
| n-C₆H₁₃ | 1 | OCH₂CF₃ | F |
| C₂H₅ | 1 | CN | H |
| n-C₃H₇ | 1 | CN | H |
| n-C₅H₁₁ | 1 | CN | H |
| n-C₆H₁₃ | 1 | CN | H |
| C₂H₅ | 0 | OCF₃ | H |
| C₂H₅ | 0 | OCF₃ | F |
| n-C₃H₇ | 0 | OCF₃ | H |
| n-C₃H₇ | 0 | OCF₃ | F |
| n-C₄H₉ | 0 | OCF₃ | H |
| n-C₄H₉ | 0 | OCF₃ | F |
| n-C₅H₁₁ | 0 | OCF₃ | H |
| n-C₅H₁₁ | 0 | OCF₃ | F |
| n-C₆H₁₃ | 0 | OCF₃ | H |
| n-C₆H₁₃ | 0 | OCF₃ | F |
| C₂H₅ | 0 | OCHF₂ | H |
| C₂H₅ | 0 | OCHF₂ | F |
| n-C₃H₇ | 0 | OCHF₂ | H |
| n-C₃H₇ | 0 | OCHF₂ | F |
| n-C₅H₁₁ | 0 | OCHF₂ | H |
| n-C₅H₁₁ | 0 | OCHF₂ | F |
| n-C₆H₁₃ | 0 | OCHF₂ | H |
| n-C₆H₁₃ | 0 | OCHF₂ | F |
| C₂H₅ | 0 | CF₃ | F |
| n-C₃H₇ | 0 | CF₃ | F |
| n-C₄H₉ | 0 | CF₃ | F |
| n-C₅H₁₁ | 0 | CF₃ | F |
| n-C₆H₁₃ | 0 | CF₃ | F |
| C₂H₅ | 0 | OCH₂F | H |
| C₂H₅ | 0 | OCH₂F | F |
| n-C₃H₇ | 0 | OCH₂F | H |
| n-C₃H₇ | 0 | OCH₂F | F |
| n-C₅H₁₁ | 0 | OCH₂F | H |
| n-C₅H₁₁ | 0 | OCH₂F | F |
| n-C₆H₁₃ | 0 | OCH₂F | H |
| n-C₆H₁₃ | 0 | OCH₂F | F |
| C₂H₅ | 0 | OCF₂Cl | H |
| C₂H₅ | 0 | OCF₂Cl | F |
| n-C₃H₇ | 0 | OCH₂Cl | H |
| n-C₃H₇ | 0 | OCH₂Cl | F |
| n-C₅H₁₁ | 0 | OCF₂Cl | H |
| n-C₅H₁₁ | 0 | OCF₂Cl | F |
| n-C₆H₁₃ | 0 | OCF₂Cl | H |
| n-C₆H₁₃ | 0 | OCF₂Cl | F |
| C₂H₅ | 0 | OCFCl₂ | H |
| C₂H₅ | 0 | OCFCl₂ | F |
| n-C₃H₇ | 0 | OCFCl₂ | H |
| n-C₃H₇ | 0 | OCFCl₂ | F |
| n-C₅H₁₁ | 0 | OCFCl₂ | H |
| n-C₅H₁₁ | 0 | OCFCl₂ | F |
| C₂H₅ | 0 | CF₂H | H |
| C₂H₅ | 0 | CF₂H | F |
| n-C₃H₇ | 0 | CF₂H | H |
| n-C₃H₇ | 0 | CF₂H | F |
| n-C₅H₁₁ | 0 | CF₂H | H |
| n-C₅H₁₁ | 0 | CF₂H | F |
| C₂H₅ | 0 | CH₂F | H |
| C₂H₅ | 0 | CH₂F | F |
| n-C₃H₇ | 0 | CH₂F | H |
| n-C₃H₇ | 0 | CH₂F | F |
| n-C₅H₁₁ | 0 | CH₂F | H |
| n-C₅H₁₁ | 0 | CH₂F | F |
| C₂H₅ | 0 | CF₂Cl | H |
| C₂H₅ | 0 | CF₂Cl | F |
| n-C₃H₇ | 0 | CF₂Cl | H |
| n-C₃H₇ | 0 | CF₂Cl | F |
| n-C₅H₁₁ | 0 | CF₂Cl | H |
| n-C₅H₁₁ | 0 | CF₂Cl | F |
| C₂H₅ | 0 | OCH₂CF₃ | H |
| C₂H₅ | 0 | OCH₂CF₃ | F |
| n-C₃H₇ | 0 | OCH₂CF₃ | H |
| n-C₃H₇ | 0 | OCH₂CF₃ | F |
| n-C₅H₁₁ | 0 | OCH₂CF₃ | H |
| n-C₅H₁₁ | 0 | OCH₂CF₃ | F |
| n-C₆H₁₃ | 0 | OCH₂CF₃ | H |
| n-C₆H₁₃ | 0 | OCH₂CF₃ | F |
| C₂H₅ | 2 | OCF₃ | H |
| C₂H₅ | 2 | OCF₃ | F |
| n-C₃H₇ | 2 | OCF₃ | H |
| n-C₃H₇ | 2 | OCF₃ | F |
| n-C₅H₁₁ | 2 | OCF₃ | H |
| n-C₅H₁₁ | 2 | OCF₃ | F |
| n-C₆H₁₃ | 2 | OCF₃ | H |
| n-C₆H₁₃ | 2 | OCF₃ | F |
| C₂H₅ | 2 | OCHF₂ | H |
| C₂H₅ | 2 | OCHF₂ | F |
| n-C₃H₇ | 2 | OCHF₂ | H |
| n-C₃H₇ | 2 | OCHF₂ | F |
| n-C₅H₁₁ | 2 | OCHF₂ | H |
| n-C₅H₁₁ | 2 | OCHF₂ | F |
| C₂H₅ | 2 | CF₃ | F |
| n-C₃H₇ | 2 | CF₃ | F |
| n-C₅H₁₁ | 2 | CF₃ | F |
| C₂H₅ | 2 | OCH₂F | H |
| C₂H₅ | 2 | OCH₂F | F |
| n-C₃H₇ | 2 | OCH₂F | H |
| n-C₃H₇ | 2 | OCH₂F | F |
| n-C₅H₁₁ | 2 | OCH₂F | H |
| n-C₅H₁₁ | 2 | OCH₂F | F |
| C₂H₅ | 2 | OCF₂Cl | H |
| C₂H₅ | 2 | OCF₂Cl | F |
| n-C₃H₇ | 2 | OCH₂Cl | H |
| n-C₃H₇ | 2 | OCH₂Cl | F |
| n-C₅H₁₁ | 2 | OCF₂Cl | H |
| n-C₅H₁₁ | 2 | OCF₂Cl | F |
| C₂H₅ | 2 | OCFCl₂ | H |
| C₂H₅ | 2 | OCFCl₂ | F |
| n-C₃H₇ | 2 | OCFCl₂ | H |
| n-C₃H₇ | 2 | OCFCl₂ | F |
| n-C₅H₁₁ | 2 | OCFCl₂ | H |
| n-C₅H₁₁ | 2 | OCFCl₂ | F |
| C₂H₅ | 2 | CF₂H | H |
| C₂H₅ | 2 | CF₂H | F |
| n-C₃H₇ | 2 | CF₂H | H |
| n-C₃H₇ | 2 | CF₂H | F |
| n-C₅H₁₁ | 2 | CF₂H | H |
| n-C₅H₁₁ | 2 | CF₂H | F |
| C₂H₅ | 2 | CH₂F | H |
| C₂H₅ | 2 | CH₂F | F |
| n-C₃H₇ | 2 | CH₂F | H |
| n-C₃H₇ | 2 | CH₂F | F |
| n-C₅H₁₁ | 2 | CH₂F | H |
| n-C₅H₁₁ | 2 | CH₂F | F |
| C₂H₅ | 2 | CF₂Cl | H |
| C₂H₅ | 2 | CF₂Cl | F |
| n-C₃H₇ | 2 | CF₂Cl | H |
| n-C₃H₇ | 2 | CF₂Cl | F |
| n-C₅H₁₁ | 2 | CF₂Cl | H |
| n-C₅H₁₁ | 2 | CF₂Cl | F |
| C₂H₅ | 2 | OCH₂CF₃ | H |
| C₂H₅ | 2 | OCH₂CF₃ | F |
| n-C₃H₇ | 2 | OCH₂CF₃ | H |
| n-C₃H₇ | 2 | OCH₂CF₃ | F |

-continued

| R | n | X | L |
|---|---|---|---|
| n-C5H11 | 2 | OCH2CF3 | H |
| n-C5H11 | 2 | OCH2CF3 | F |

Example 3

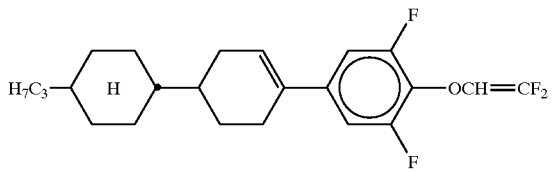

170 mmol of 3,5-difluoro-2,2,2-trifluoroethoxy-4-bromobenzene are dissolved in 350 ml of diethyl ether, and the solution is cooled to −70° C. with stirring. 170 mmol of n-BuLi are added dropwise to the cooled solution. The mixture is stirred for 0.5 hour, and trans-4-[trans-4-propylcyclohexyl]cyclohexanone in 50 ml of diethyl ether is then added dropwise to the solution cooled to −70° C. The reaction mixture is allowed to warm to room temperature, water is added, and the mixture is acidified by means of dilute HCl. The mixture is subsequently extracted with methyl tert-butyl ether and subjected to customary work-up. The product (55 mmol) is dissolved in 50 ml of THF. 55 mmol of LDA are added dropwise at −70° C. The mixture is allowed to warm to −30° C. with stirring and is then subjected to customary work-up.

The following compounds of the formula

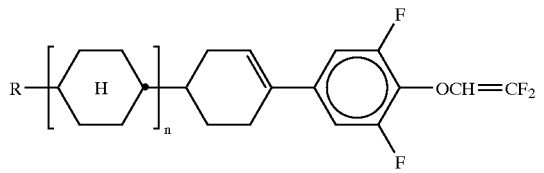

are prepared analogously:

| R | n | L |
|---|---|---|
| CH3 | 1 | H |
| CH3 | 1 | F |
| C2H5 | 1 | H |
| C2H5 | 1 | F |
| n-C4H9 | 1 | H |
| n-C4H9 | 1 | F |
| n-C5H11 | 1 | H |
| n-C5H11 | 1 | F |
| n-C6H13 | 1 | H |
| n-C6H13 | 1 | H |
| C2H5 | 0 | H |
| C2H5 | 0 | F |
| n-C3H7 | 0 | H |
| n-C3H7 | 0 | F |
| n-C5H11 | 0 | H |
| n-C5H11 | 0 | F |
| n-C6H13 | 0 | H |
| n-C6H13 | 0 | H |
| C2H5 | 2 | H |
| C2H5 | 2 | F |

-continued

| R | n | L |
|---|---|---|
| n-C3H7 | 2 | H |
| n-C3H7 | 2 | F |
| n-C5H11 | 2 | H |
| n-C5H11 | 2 | F |
| n-C6H13 | 2 | H |
| n-C6H13 | 2 | H |

Example 4

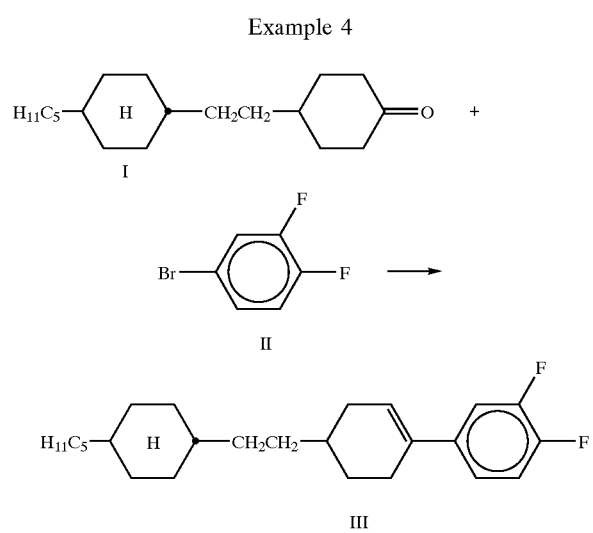

0.08 mol of 2,6-difluoro-4-bromobenzene (II) are dissolved in 100 ml of diethyl ether, and 0.08 mol of n-BuLi is added at from −30 to −40° C. The mixture is stirred for a further 15 minutes, and 0.08 mol of 1-[trans-4-(trans-4-propylcyclohexyl)]-2-[cyclohexanone]ethane (I) in 30 ml of diethyl ether is then added dropwise at from −25 to −20° C. The mixture is stirred for a further one hour without cooling, during which the solution warms to room temperature. The product is hydrolyzed by means of saturated ammonium chloride solution, the mixture is acidified by means of 10% hydrochloric acid, and the organic phase is separated off and subjected to customary work-up. The product is dissolved in 120 ml of toluene, 3 g of p-toluenesulfonic acid are added, and the mixture is boiled for 1 hour on a water separator. The reaction mixture is then washed with water and saturated sodium chloride solution and subjected to customary work-up.

The following compounds of the formula

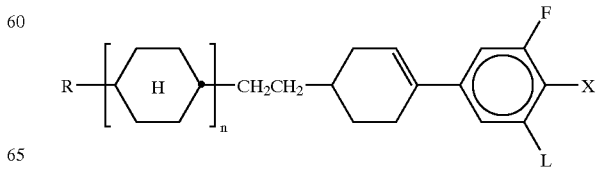

are prepared analogously:

| R | n | X | L |
|---|---|---|---|
| C₂H₅ | 1 | OCF₃ | H |
| C₂H₅ | 1 | OCF₃ | F |
| n-C₄H₉ | 1 | OCF₃ | H |
| n-C₄H₉ | 1 | OCF₃ | F |
| n-C₅H₁₁ | 1 | OCF₃ | H |
| n-C₅H₁₁ | 1 | OCF₃ | F |
| n-C₆H₁₃ | 1 | OCF₃ | H |
| n-C₆H₁₃ | 1 | OCF₃ | F |
| C₂H₅ | 1 | OCHF₂ | H |
| C₂H₅ | 1 | OCHF₂ | F |
| n-C₃H₇ | 1 | OCHF₂ | H |
| n-C₃H₇ | 1 | OCHF₂ | F |
| n-C₅H₁₁ | 1 | OCHF₂ | H |
| n-C₅H₁₁ | 1 | OCHF₂ | F |
| n-C₆H₁₃ | 1 | OCHF₂ | H |
| n-C₆H₁₃ | 1 | OCHF₂ | F |
| C₂H₅ | 1 | CF₃ | H |
| C₂H₅ | 1 | CF₃ | F |
| n-C₃H₇ | 1 | CF₃ | H |
| n-C₃H₇ | 1 | CF₃ | F |
| n-C₅H₁₁ | 1 | CF₃ | H |
| n-C₅H₁₁ | 1 | CF₃ | F |
| n-C₆H₁₃ | 1 | CF₃ | H |
| n-C₆H₁₃ | 1 | CF₃ | F |
| C₂H₅ | 1 | F | H |
| C₂H₅ | 1 | F | F |
| n-C₄H₉ | 1 | F | H |
| n-C₄H₉ | 1 | F | F |
| n-C₅H₁₁ | 1 | F | H |
| n-C₅H₁₁ | 1 | F | F |
| n-C₆H₁₃ | 1 | F | H |
| n-C₆H₁₃ | 1 | F | F |
| C₂H₅ | 1 | Cl | H |
| C₂H₅ | 1 | Cl | F |
| n-C₃H₇ | 1 | Cl | H |
| n-C₃H₇ | 1 | Cl | F |
| n-C₅H₁₁ | 1 | Cl | H |
| n-C₅H₁₁ | 1 | Cl | F |
| n-C₆H₁₃ | 1 | Cl | H |
| n-C₆H₁₃ | 1 | Cl | F |
| C₂H₅ | 1 | OCH₂F | H |
| C₂H₅ | 1 | OCH₂F | F |
| n-C₃H₇ | 1 | OCH₂F | H |
| n-C₃H₇ | 1 | OCH₂F | F |
| n-C₅H₁₁ | 1 | OCH₂F | H |
| n-C₅H₁₁ | 1 | OCH₂F | F |
| n-C₆H₁₃ | 1 | OCH₂F | H |
| n-C₆H₁₃ | 1 | OCH₂F | F |
| n-C₃H₇ | 1 | CH=CF₂ | H |
| n-C₃H₇ | 1 | CH=CF₂ | F |
| n-C₅H₁₁ | 1 | CH=CF₂ | H |
| n-C₅H₁₁ | 1 | CH=CF₂ | F |
| n-C₃H₇ | 1 | CF=CF₂ | H |
| n-C₃H₇ | 1 | CF=CF₂ | F |
| n-C₅H₁₁ | 1 | CF=CF₂ | H |
| n-C₅H₁₁ | 1 | CF=CF₂ | F |
| n-C₃H₇ | 1 | CF=CHF | H |
| n-C₃H₇ | 1 | CF=CHF | F |
| n-C₅H₁₁ | 1 | CF=CHF | H |
| n-C₅H₁₁ | 1 | CF=CHF | F |
| C₂H₅ | 1 | OCF₂Cl | H |
| C₂H₅ | 1 | OCF₂Cl | F |
| n-C₃H₇ | 1 | OCH₂Cl | H |
| n-C₃H₇ | 1 | OCH₂Cl | F |
| n-C₅H₁₁ | 1 | OCF₂Cl | H |
| n-C₅H₁₁ | 1 | OCF₂Cl | F |
| C₂H₅ | 1 | OCFCl₂ | H |
| C₂H₅ | 1 | OCFCl₂ | F |
| n-C₃H₇ | 1 | OCFCl₂ | H |
| n-C₃H₇ | 1 | OCFCl₂ | F |
| n-C₅H₁₁ | 1 | OCFCl₂ | H |
| n-C₅H₁₁ | 1 | OCFCl₂ | F |
| C₂H₅ | 1 | CF₂H | H |
| C₂H₅ | 1 | CF₂H | F |
| n-C₃H₇ | 1 | CF₂H | H |

-continued

| R | n | X | L |
|---|---|---|---|
| n-C₃H₇ | 1 | CF₂H | F |
| n-C₅H₁₁ | 1 | CF₂H | H |
| n-C₅H₁₁ | 1 | CF₂H | F |
| n-C₆H₁₃ | 1 | CF₂H | H |
| n-C₆H₁₃ | 1 | CF₂H | F |
| C₂H₅ | 1 | CH₂F | H |
| C₂H₅ | 1 | CH₂F | F |
| n-C₃H₇ | 1 | CH₂F | H |
| n-C₃H₇ | 1 | CH₂F | F |
| n-C₅H₁₁ | 1 | CH₂F | H |
| n-C₅H₁₁ | 1 | CH₂F | F |
| n-C₆H₁₃ | 1 | CH₂F | H |
| n-C₆H₁₃ | 1 | CH₂F | F |
| C₂H₅ | 1 | CF₂Cl | H |
| C₂H₅ | 1 | CF₂Cl | F |
| n-C₃H₇ | 1 | CF₂Cl | H |
| n-C₃H₇ | 1 | CF₂Cl | F |
| n-C₅H₁₁ | 1 | CF₂Cl | H |
| n-C₅H₁₁ | 1 | CF₂Cl | F |
| n-C₆H₁₃ | 1 | CF₂Cl | H |
| n-C₆H₁₃ | 1 | CF₂Cl | F |
| C₂H₅ | 1 | CN | H |
| C₂H₅ | 1 | CN | F |
| n-C₃H₇ | 1 | CN | H |
| n-C₃H₇ | 1 | CN | F |
| n-C₅H₁₁ | 1 | CN | H |
| n-C₅H₁₁ | 1 | CN | F |
| n-C₆H₁₃ | 1 | CN | H |
| n-C₆H₁₃ | 1 | CN | F |
| C₂H₅ | 1 | OCH₂CF₃ | H |
| C₂H₅ | 1 | OCH₂CF₃ | F |
| n-C₃H₇ | 1 | OCH₂CF₃ | H |
| n-C₃H₇ | 1 | OCH₂CF₃ | F |
| n-C₅H₁₁ | 1 | OCH₂CF₃ | H |
| n-C₅H₁₁ | 1 | OCH₂CF₃ | F |
| n-C₆H₁₃ | 1 | OCH₂CF₃ | H |
| n-C₆H₁₃ | 1 | OCH₂CF₃ | F |
| C₂H₅ | 1 | OCH=CF₂ | H |
| C₂H₅ | 1 | OCH=CF₂ | F |
| n-C₃H₇ | 1 | OCH=CF₂ | H |
| n-C₃H₇ | 1 | OCH=CF₂ | F |
| n-C₅H₁₁ | 1 | OCH=CF₂ | H |
| n-C₅H₁₁ | 1 | OCH=CF₂ | F |
| n-C₆H₁₃ | 1 | OCH=CF₂ | H |
| n-C₆H₁₃ | 1 | OCH=CF₂ | F |
| C₂H₅ | 2 | OCF₃ | H |
| C₂H₅ | 2 | OCF₃ | F |
| n-C₃H₇ | 2 | OCF₃ | H |
| n-C₃H₇ | 2 | OCF₃ | F |
| n-C₅H₁₁ | 2 | OCF₃ | H |
| n-C₅H₁₁ | 2 | OCF₃ | F |
| C₂H₅ | 2 | OCHF₂ | H |
| C₂H₅ | 2 | OCHF₂ | F |
| n-C₃H₇ | 2 | OCHF₂ | H |
| n-C₃H₇ | 2 | OCHF₂ | F |
| n-C₄H₉ | 2 | OCHF₂ | H |
| n-C₄H₉ | 2 | OCHF₂ | F |
| n-C₅H₁₁ | 2 | OCHF₂ | H |
| n-C₅H₁₁ | 2 | OCHF₂ | F |
| n-C₆H₁₃ | 2 | OCHF₂ | H |
| n-C₆H₁₃ | 2 | OCHF₂ | F |
| C₂H₅ | 2 | CF₃ | H |
| C₂H₅ | 2 | CF₃ | F |
| n-C₃H₇ | 2 | CF₃ | H |
| n-C₃H₇ | 2 | CF₃ | F |
| n-C₄H₉ | 2 | CF₃ | H |
| n-C₄H₉ | 2 | CF₃ | F |
| n-C₅H₁₁ | 2 | CF₃ | H |
| n-C₅H₁₁ | 2 | CF₃ | F |
| n-C₆H₁₃ | 2 | CF₃ | H |
| n-C₆H₁₃ | 2 | CF₃ | F |
| C₂H₅ | 2 | OCH₂F | H |
| C₂H₅ | 2 | OCH₂F | F |
| n-C₃H₇ | 2 | OCH₂F | H |
| n-C₃H₇ | 2 | OCH₂F | F |
| n-C₄H₉ | 2 | OCH₂F | H |
| n-C₄H₉ | 2 | OCH₂F | F |

-continued

| R | n | X | L |
|---|---|---|---|
| n-C$_5$H$_{11}$ | 2 | OCH$_2$F | H |
| n-C$_5$H$_{11}$ | 2 | OCH$_2$F | F |
| n-C$_6$H$_{13}$ | 2 | OCH$_2$F | H |
| n-C$_6$H$_{13}$ | 2 | OCH$_2$F | F |
| C$_2$H$_5$ | 2 | OCF$_2$Cl | H |
| C$_2$H$_5$ | 2 | OCF$_2$Cl | F |
| n-C$_3$H$_7$ | 2 | OCH$_2$Cl | H |
| n-C$_3$H$_7$ | 2 | OCH$_2$Cl | F |
| n-C$_4$H$_9$ | 2 | OCF$_2$Cl | H |
| n-C$_4$H$_9$ | 2 | OCF$_2$Cl | F |
| n-C$_5$H$_{11}$ | 2 | OCF$_2$Cl | H |
| n-C$_5$H$_{11}$ | 2 | OCF$_2$Cl | F |
| n-C$_6$H$_{13}$ | 2 | OCF$_2$Cl | H |
| n-C$_6$H$_{13}$ | 2 | OCF$_2$Cl | F |
| C$_2$H$_5$ | 2 | OCFCl$_2$ | H |
| C$_2$H$_5$ | 2 | OCFCl$_2$ | F |
| n-C$_3$H$_7$ | 2 | OCFCl$_2$ | H |
| n-C$_3$H$_7$ | 2 | OCFCl$_2$ | F |
| n-C$_4$H$_9$ | 2 | OCFCl$_2$ | H |
| n-C$_4$H$_9$ | 2 | OCFCl$_2$ | F |
| n-C$_5$H$_{11}$ | 2 | OCFCl$_2$ | H |
| n-C$_5$H$_{11}$ | 2 | OCFCl$_2$ | F |
| n-C$_6$H$_{13}$ | 2 | OCFCl$_2$ | H |
| n-C$_6$H$_{13}$ | 2 | OCFCl$_2$ | F |
| C$_2$H$_5$ | 2 | CF$_2$H | H |
| C$_2$H$_5$ | 2 | CF$_2$H | F |
| n-C$_3$H$_7$ | 2 | CF$_2$H | H |
| n-C$_3$H$_7$ | 2 | CF$_2$H | F |
| n-C$_4$H$_9$ | 2 | CF$_2$H | H |
| n-C$_4$H$_9$ | 2 | CF$_2$H | F |
| n-C$_5$H$_{11}$ | 2 | CF$_2$H | H |
| n-C$_5$H$_{11}$ | 2 | CF$_2$H | F |
| n-C$_6$H$_{13}$ | 2 | CF$_2$H | H |
| n-C$_6$H$_{13}$ | 2 | CF$_2$H | F |
| C$_2$H$_5$ | 2 | CH$_2$F | H |
| C$_2$H$_5$ | 2 | CH$_2$F | F |
| n-C$_3$H$_7$ | 2 | CH$_2$F | H |
| n-C$_3$H$_7$ | 2 | CH$_2$F | F |
| n-C$_4$H$_9$ | 2 | CH$_2$F | H |
| n-C$_4$H$_9$ | 2 | CH$_2$F | F |
| n-C$_5$H$_{11}$ | 2 | CH$_2$F | H |
| n-C$_5$H$_{11}$ | 2 | CH$_2$F | F |
| n-C$_6$H$_{13}$ | 2 | CH$_2$F | H |
| n-C$_6$H$_{13}$ | 2 | CH$_2$F | F |
| C$_2$H$_5$ | 2 | CN | H |
| C$_2$H$_5$ | 2 | CN | F |
| n-C$_3$H$_7$ | 2 | CN | H |
| n-C$_3$H$_7$ | 2 | CN | F |
| n-C$_4$H$_9$ | 2 | CN | H |
| n-C$_4$H$_9$ | 2 | CN | F |
| n-C$_5$H$_{11}$ | 2 | CN | H |
| n-C$_5$H$_{11}$ | 2 | CN | F |
| n-C$_6$H$_{13}$ | 2 | CN | H |
| n-C$_6$H$_{13}$ | 2 | CN | F |

MIXTURE EXAMPLES

Example A

| | | | |
|---|---|---|---|
| PCH-5F | 5.0% | Clearing point [° C.]: | +94 |
| PCH-7F | 6.0% | Δn[589 nm, 20° C.]: | +0.0849 |
| CCP-2OCF$_3$ | 11.0% | V$_{(10,0,020)}$[V]: | 1.63 |
| CCP-3OCF$_3$ | 12.0% | V$_{(50,0,20)}$[V]: | 2.05 |
| CCP-4OCF$_3$ | 10.0% | V$_{(50,0,20)}$[V]: | 2.58 |
| CCP-5OCF$_3$ | 12.0% | | |
| CCP-3F.F.F | 12.0% | | |
| CCP-5F.F.F | 9.0% | | |
| CLU-3F | 12.0% | | |
| CLU-5F | 11.0% | | |

Example B

| | | | |
|---|---|---|---|
| PCH-5F | 9.0% | Clearing point [° C.]: | +94 |
| PCH-6F | 7.2% | Δn[589 nm, 20° C.]: | +0.0849 |
| PCH-7F | 5.4% | Δε 1 kHz, 20° C.]: | 5.40 |
| CCP-20CF$_3$ | 7.2% | | |
| CCP-30CF$_3$ | 10.8% | | |
| CCP-40CF$_3$ | 8.1% | | |
| CCP-50CF$_3$ | 8.1% | | |
| BCH-3F.F | 10.8% | | |
| BCH-5F.F | 9.0% | | |
| ECCP-30CF$_3$ | 4.5% | | |
| ECCP-50CF$_3$ | 4.5% | | |
| CBC-33F | 1.8% | | |
| CBC-53F | 1.8% | | |
| CBC-55F | 1.8% | | |
| CLG-3-F | 10.0% | | |

Example C

| | | | |
|---|---|---|---|
| PCH-5F | 9.0% | Clearing point [° C.]: | +91.2 |
| PCH-6F | 7.2% | Δn[589 nm, 20° C.]: | +0.0974 |
| PCH-7F | 5.4% | Δε[1 kHz, 20° C.]: | 5.80 |
| CCP-20CF$_3$ | 7.2% | | |
| CCP-30CF$_3$ | 10.8% | | |
| CCP-40CF$_3$ | 8.1% | | |
| CCP-50CF$_3$ | 8.1% | | |
| BCH-3F.F | 10.8% | | |
| BCH-5F.F | 9.00% | | |
| ECCP-30CF$_3$ | 4.5% | | |
| ECCP-50CF$_3$ | 4.5% | | |
| CBC-33F | 1.8% | | |
| CBC-53F | 1.8% | | |
| CBC-55F | 1.8% | | |
| CLU-3-F | 10.0% | | |

Example D

| | | | |
|---|---|---|---|
| PCH-5F | 9.0% | Clearing point [° C.]: | +92.2 |
| PCH-6F | 7.2% | Δn[589 nm, 20° C.]: | +0.0969 |
| PCH-7F | 5.4% | Δε[1 kHz, 20° C.]: | 5.67 |
| CCP-20CF$_3$ | 7.2% | | |
| CCP-30CF$_3$ | 10.8% | | |
| CCP-40CF$_3$ | 8.1% | | |
| CCP-50CF$_3$ | 8.1% | | |
| BCH-3F.F | 10.8% | | |
| BCH-5F.F | 9.0% | | |
| ECCP-30CF$_3$ | 4.5% | | |
| ECCP-50CF$_3$ | 4.5% | | |
| CBC-33F | 1.8% | | |
| CBC-53F | 1.8% | | |
| CBC-55F | 1.8% | | |
| CLU-5-F | 10.0% | | |

Example E

| | | | |
|---|---|---|---|
| PCH-5F | 9.0% | Clearing point [° C.]: | +74.2 |
| PCH-6F | 7.2% | Δn[589 nm, 20° C.]: | +0.0919 |
| PCH-7F | 5.4% | Δε[1 kHz, 20° C.]: | 5.51 |
| CCP-20CF$_3$ | 7.2% | | |
| CCP-30CF$_3$ | 10.8% | | |
| CCP-40CF$_3$ | 8.1% | | |
| CCP-50CF$_3$ | 8.1% | | |
| BCH-3F.F | 10.8% | | |
| BCH-5F.F | 9.0% | | |

-continued

| | |
|---|---|
| ECCP-30CF$_3$ | 4.5% |
| ECCP-50CF$_3$ | 4.5% |
| CBC-33F | 1.8% |
| CBC-53F | 1.8% |
| CBC-55F | 1.8% |
| CLU-0-F | 10.0% |

Example F

| | | | |
|---|---|---|---|
| PCH-5F | 9.0% | Clearing point [° C.]: | +109.3 |
| PCH-6F | 7.2% | Δn[589 nm, 20° C.]: | +0.0980 |
| PCH-7F | 5.4% | Δε[1 kHz, 20° C.]: | 5.76 |
| CCP-20CF$_3$ | 7.2% | | |
| CCP-30CF$_3$ | 10.8% | | |
| CCP-40CF$_3$ | 8.1% | | |
| CCP-50CF$_3$ | 8.1% | | |
| BCH-3F.F | 10.8% | | |
| BCH-5F.F | 9.0% | | |
| ECCP-30CF$_3$ | 4.5% | | |
| ECCP-50CF$_3$ | 4.5% | | |
| CBC-33F | 1.8% | | |
| CBC-53F | 1.8% | | |
| CBC-55F | 1.8% | | |
| CCLU-3-F | 10.0% | | |

Example G

| | | | |
|---|---|---|---|
| PCH-5F | 9.0% | Clearing point [° C.]: | +96 |
| PCH-6F | 7.2% | Δn[589 nm, 20° C.]: | +0.0983 |
| PCH-7F | 5.4% | Δε[1 kHz, 20° C.]: | 5.83 |
| CCP-20CF$_3$ | 7.2% | | |
| CCP-30CF$_3$ | 10.8% | | |
| CCP-40CF$_3$ | 8.1% | | |
| CCP-50CF$_3$ | 8.1% | | |
| BCH-3F.F | 10.8% | | |
| BCH-5F.F | 9.0% | | |
| ECCP-30CF$_3$ | 4.5% | | |
| ECCP-50CF$_3$ | 4.5% | | |
| CBC-33F | 1.8% | | |
| CBC-53F | 1.8% | | |
| CBC-55F | 1.8% | | |
| CLU-3-OM | 10.0% | | |

Example H

| | | | |
|---|---|---|---|
| PCH-5F | 9.0% | Clearing point [° C.]: | +87.6 |
| PCH-6F | 7.2% | Δn[589 nm, 20° C.]: | +0.0960 |
| PCH-7F | 5.4% | Δε[1 kHz, 20° C.]: | 5.81 |
| CCP-20CF$_3$ | 7.2% | | |
| CCP-30CF$_3$ | 10.8% | | |
| CCP-40CF$_3$ | 8.1% | | |
| CCP-50CF$_3$ | 8.1% | | |
| BCH-3F.F | 10.8% | | |
| BCH-5F.F | 9.0% | | |
| ECCP-30CF$_3$ | 4.5% | | |
| ECCP-50CF$_3$ | 4.5% | | |
| CBC-33F | 1.8% | | |
| CBC-53F | 1.8% | | |
| CBC-55F | 1.8% | | |
| CLU-2-F | 10.0% | | |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A liquid-crystalline medium based on a mixture of polar compounds having positive dielectric anisotropy, comprising at least one fluorophenylcyclohexene derivative of formula I

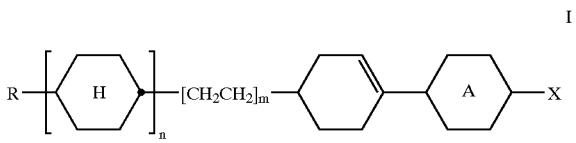

wherein

R is H, an unsubstituted alkyl or alkenyl radical having up to 18 carbon atoms, in which one or more non-adjacent $CH_2$ groups are optionally replaced by —O—, —S—, —CO—, —O—CO—, —CO—O— or —C≡C—,

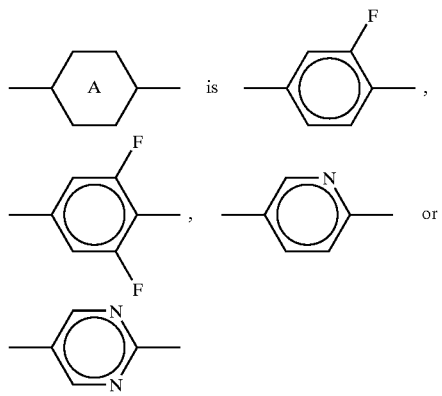

X is CN or Q—Y,

Y is H, F or Cl,

Q is —$CF_2$—, —CHF—, —$OCF_2$—, —OCHF—, —$OCH_2CF_2$—, —CH=CF—, —CF=CH—, —CF=CF—, —O—CF=CF—, —O—CH=CF— or a single bond, m is 0 or 1, and n is 0, 1 or 2.

2. A medium according to claim 1, further comprising at least one compound of formulae II, III or IV:

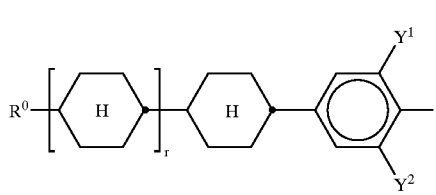

-continued

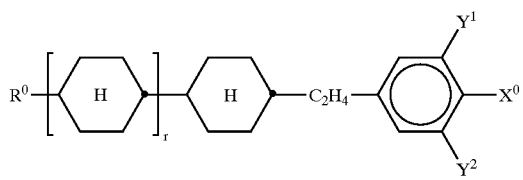

III

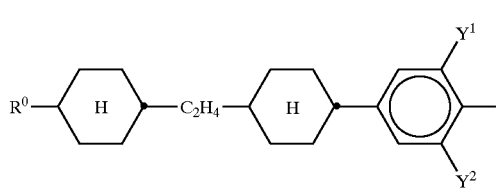

IV wherein
- $R^0$ is alkyl, oxaalkyl, fluoroalkyl or alkenyl, in each case having up to 7 carbon atoms,
- $X^0$ is F, Cl, $CF_3$, $OCF_3$, $OCHF_2$ or CN,
- $Y^1$ and $Y^2$ are each, independently of one another, H or F, and
- r is 0 or 1.

3. A medium according to claim 1, further comprising at least one compound of general formula V to VIII:

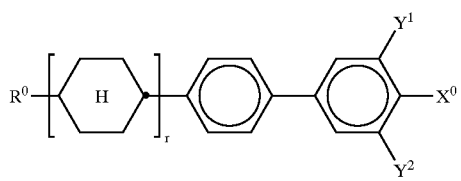

V

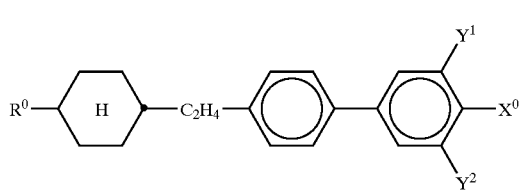

VI

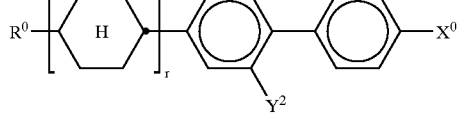

VII

VIII wherein
- $R^0$ is alkyl, oxaalkyl, fluoroalkyl or alkenyl, in each case having up to 7 carbon atoms,
- $X^0$ is F, Cl, $CF_3$, $OCF_3$, $OCHF_2$ or CN,
- $Y^1$ and $Y^2$ are each, independently of one another, H or F, and
- r is 0 or 1.

4. A medium according to claim 1, further comprising at least one compound of formulae IX to XII:

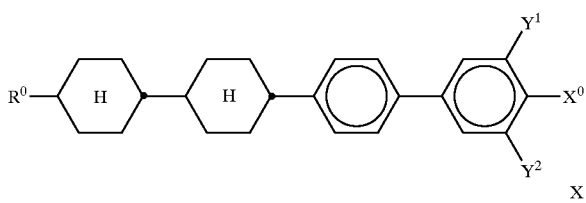

IX

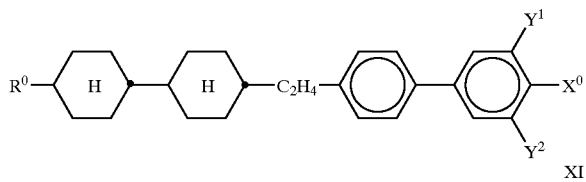

X

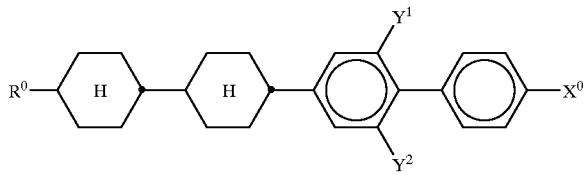

XI or

XII wherein
- $R^0$ is alkyl, oxaalkyl, fluoroalkyl or alkenyl, in each case having up to 7 carbon atoms,
- $X^0$ is F, Cl, $CF_3$, $OCF_3$, $OCHF_2$ or CN, and
- $Y^1$ and $Y^2$ are each, independently of one another, H or F.

5. A medium according to claim 1, further comprising at least one compound of formulae XIII to XV:

XIII

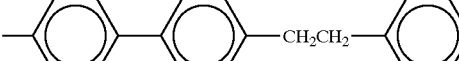

XIV or

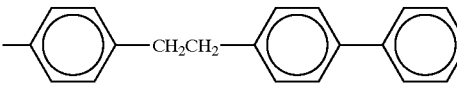

XV

- $R^0$ is alkyl, oxaalkyl, fluoroalkyl or alkenyl, in each case having up to 7 carbon atoms, and
- $X^0$ is F, Cl, $CF_3$, $OCF_3$, $OCHF_2$ or CN.

6. A medium according to claim 2, wherein the proportion of compounds of the formulae I to IV together in the total mixture is at least 50% by weight.

7. A medium according to claim 1, wherein the proportion of compounds of the formula I in the total mixture is 10 to 50% by weight.

8. A medium according to claim 2, wherein the proportion of compounds of formulae II to IV in the total mixture is 30 to 70% by weight.

9. A liquid-crystalline medium, consisting essentially of at least one compound of formula I

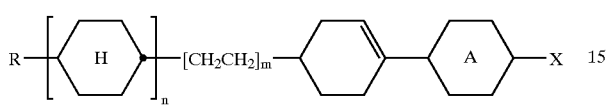

I wherein

R is H, an unsubstituted alkyl or alkenyl radical having up to 18 carbon atoms, in which one or more non-adjacent CH$_2$ groups are optionally replaced b —O—, —S—, —CO—, —O—CO—, —CO—O—, or —C≡C,

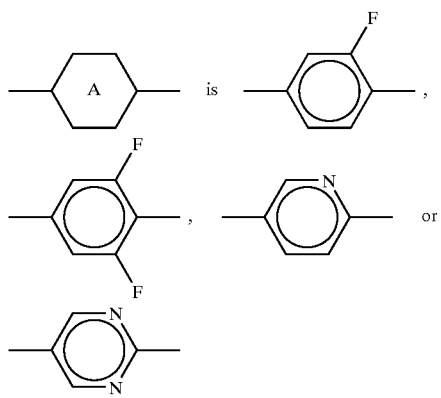

X is CN or Q—Y,
Y is H, F or Cl,
Q is —CF$_2$—, —CHF—, —OCF$_2$—, —OCHF—, —OCH$_2$CF$_2$—, —CH=CF—, —CF=CH—, —CF=CF—, —O—CF=CF—, —O—CH=CF— or a single bond,
m is 0 or 1, and
n is 0, 1 or 2,
and at least one compound of formulae II to XV:

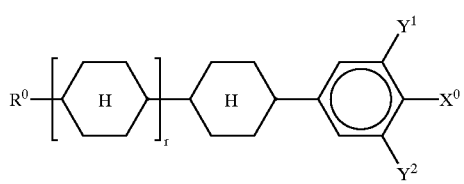

II

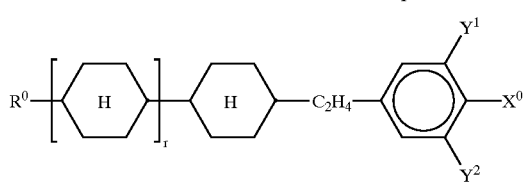

III

-continued

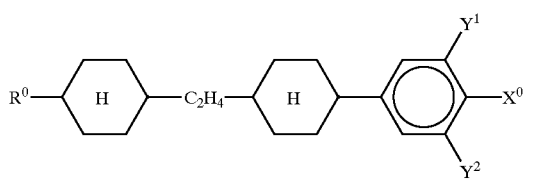

IV

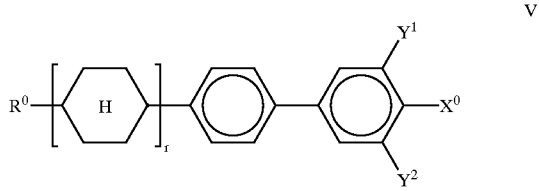

V

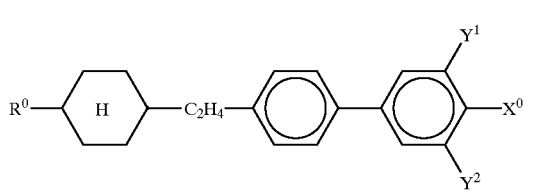

VI

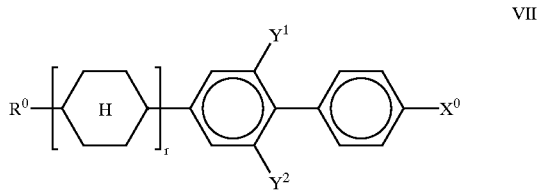

VII

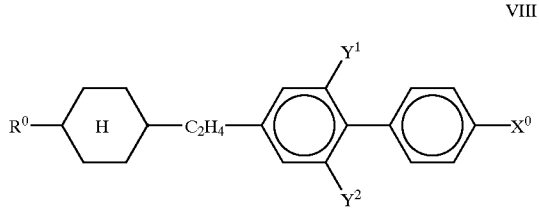

VIII

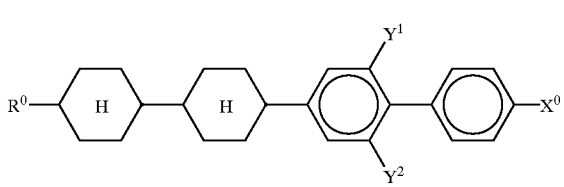

IX

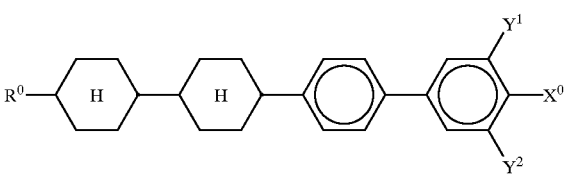

X

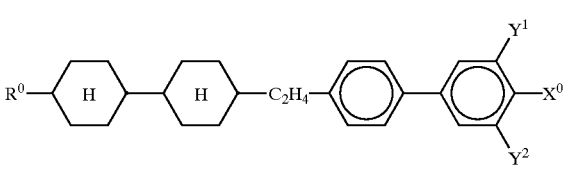

XI

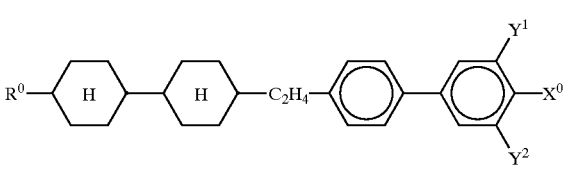

-continued

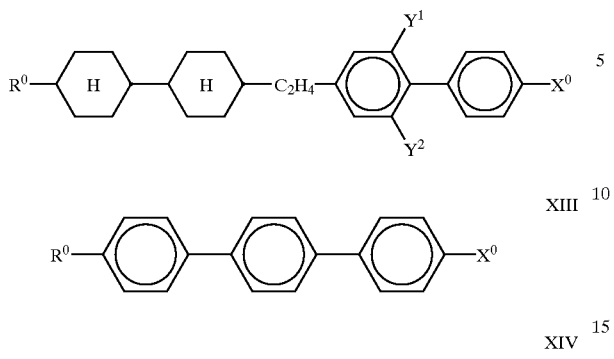

wherein
- R⁰ is alkyl, oxaalkyl, fluoroalkyl or alkenyl, in each case having up to 7 carbon atoms,
- X⁰ is F, Cl, CF₃, OCF₃, OCHF₂ or CN,
- Y¹ and Y² are each, independently of one another, H or F, an
- r is 0 or 1.

10. A liquid-crystalline medium according to claim 1, comprising a fluorophenylcyclohexene derivative of the formula

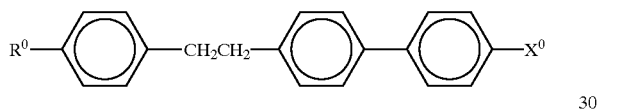

wherein
L is H or F.

11. A liquid-crystalline medium according to claim 1, comprising a fluorophenylcyclohexene derivative of formula I2

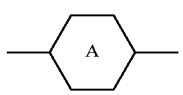

12. An electro-optical liquid-crystal display containing a liquid-crystalline medium according to claim 1.

13. A medium according to claim 1, wherein

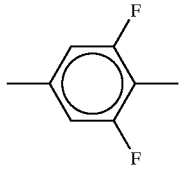

X is Q—Y, Y is F and Q is a single bond.

* * * * *

UNITED STATES PATENT AND TRADEMARK OFFICE
CERTIFICATE OF CORRECTION

PATENT NO. : 6,689,291 B1 Page 1 of 1
APPLICATION NO. : 08/225267
DATED : February 10, 2004
INVENTOR(S) : Reiffenrath et al.

It is certified that error appears in the above-identified patent and that said Letters Patent is hereby corrected as shown below:

Column 45, line 22 reads "b," should read -- by --
Column 47, line 38 reads "an," should read -- and --

Signed and Sealed this

Twenty-ninth Day of August, 2006

JON W. DUDAS
*Director of the United States Patent and Trademark Office*